US011948665B2

(12) United States Patent
Madani et al.

(10) Patent No.: US 11,948,665 B2
(45) **Date of Patent: *Apr. 2, 2024**

(54) SYSTEMS AND METHODS FOR LANGUAGE MODELING OF PROTEIN ENGINEERING

(71) Applicant: Salesforce, Inc., San Francisco, CA (US)

(72) Inventors: Ali Madani, San Francisco, CA (US); Bryan McCann, Menlo Park, CA (US); Nikhil Naik, Mountain View, CA (US)

(73) Assignee: Salesforce, Inc., San Francisco, CA (US)

( * ) Notice: Subject to any disclaimer, the term of this patent is extended or adjusted under 35 U.S.C. 154(b) by 696 days.

This patent is subject to a terminal disclaimer.

(21) Appl. No.: 17/001,068

(22) Filed: Aug. 24, 2020

(65) Prior Publication Data

US 2021/0249100 A1 Aug. 12, 2021

Related U.S. Application Data

(60) Provisional application No. 62/971,119, filed on Feb. 6, 2020.

(51) Int. Cl.

| | |
|---|---|
| ***G16B 40/30*** | (2019.01) |
| ***G06F 30/20*** | (2020.01) |
| ***G06F 111/08*** | (2020.01) |
| ***G16B 5/20*** | (2019.01) |
| ***G16B 15/20*** | (2019.01) |
| ***G16B 25/10*** | (2019.01) |
| ***G16B 30/00*** | (2019.01) |
| ***G16B 40/20*** | (2019.01) |
| ***G16B 50/10*** | (2019.01) |

(52) U.S. Cl.

CPC ............. *G16B 40/30* (2019.02); *G06F 30/20* (2020.01); *G16B 5/20* (2019.02); *G16B 15/20* (2019.02); *G16B 25/10* (2019.02); *G16B 30/00* (2019.02); *G16B 40/20* (2019.02); *G16B 50/10* (2019.02); *G06F 2111/08* (2020.01)

(58) Field of Classification Search

None

See application file for complete search history.

(56) References Cited

U.S. PATENT DOCUMENTS

| | | | |
|---|---|---|---|
| 10,282,663 | B2 | 5/2019 | Socher et al. |
| 10,474,709 | B2 | 11/2019 | Paulus |
| 10,521,465 | B2 | 12/2019 | Paulus |
| 10,542,270 | B2 | 1/2020 | Zhou et al. |
| 10,558,750 | B2 | 2/2020 | Lu et al. |
| 10,565,305 | B2 | 2/2020 | Lu et al. |
| 10,565,306 | B2 | 2/2020 | Lu et al. |
| 10,565,318 | B2 | 2/2020 | Bradbury |
| 10,565,493 | B2 | 2/2020 | Merity et al. |
| 10,573,295 | B2 | 2/2020 | Zhou et al. |
| 10,592,767 | B2 | 3/2020 | Trott et al. |
| 10,699,060 | B2 | 6/2020 | Mccann |
| 10,747,761 | B2 | 8/2020 | Zhong et al. |
| 10,776,581 | B2 | 9/2020 | Mccann et al. |
| 10,783,875 | B2 | 9/2020 | Hosseini-Asl et al. |
| 10,817,650 | B2 | 10/2020 | Mccann et al. |
| 10,839,284 | B2 | 11/2020 | Hashimoto et al. |
| 10,846,478 | B2 | 11/2020 | Lu et al. |
| 2016/0350653 | A1 | 12/2016 | Socher et al. |
| 2017/0024645 | A1 | 1/2017 | Socher et al. |
| 2017/0032280 | A1 | 2/2017 | Socher |
| 2017/0140240 | A1 | 5/2017 | Socher et al. |
| 2018/0096219 | A1 | 4/2018 | Socher |
| 2018/0121788 | A1 | 5/2018 | Hashimoto et al. |
| 2018/0121799 | A1 | 5/2018 | Hashimoto et al. |
| 2018/0129931 | A1 | 5/2018 | Bradbury et al. |
| 2018/0129937 | A1 | 5/2018 | Bradbury et al. |
| 2018/0129938 | A1 | 5/2018 | Xiong et al. |
| 2018/0268287 | A1 | 9/2018 | Johansen et al. |
| 2018/0268298 | A1 | 9/2018 | Johansen et al. |
| 2018/0336453 | A1 | 11/2018 | Merity et al. |
| 2018/0373987 | A1 | 12/2018 | Zhang et al. |
| 2019/0130248 | A1 | 5/2019 | Zhong et al. |
| 2019/0130249 | A1 | 5/2019 | Bradbury et al. |
| 2019/0130273 | A1 | 5/2019 | Keskar et al. |
| 2019/0130312 | A1 | 5/2019 | Xiong et al. |
| 2019/0130896 | A1 | 5/2019 | Zhou et al. |
| 2019/0188568 | A1 | 6/2019 | Keskar et al. |
| 2019/0213482 | A1 | 7/2019 | Socher et al. |
| 2019/0251431 | A1 | 8/2019 | Keskar et al. |
| 2019/0258714 | A1 | 8/2019 | Zhong et al. |
| 2019/0258939 | A1 | 8/2019 | Min et al. |

(Continued)

OTHER PUBLICATIONS

Madani A. Machine Learning for Structural Biology Workshop, NeurIPS 2020. pp. 1-19. (Year: 2020).*

Bileschi ML. bioRxiv 626507, pp. 1-29. (Year: 2019).*

Busia A. arXiv 1702.03865, p. 1-11. (Year: 2017).*

Koohi-Moghadam M. Nature Machine Intelligence 1, 561-567. (Year: 2019).*

Li Y. arXiv :1810.06339, pp. 1-150. (Year: 2018).*

Karp PD. Bioinformatics 17(6): 526-532. (Year: 2001).*

Das S. Knowledge Discovery in Databases: PKDD 2007. PKDD 2007. Lecture Notes in Computer Science 4702. Springer, Berlin, Heidelberg. pp. 54-66. (Year: 2007).*

Guo Y. BMC Bioinformatics 20: 341. pp. 1-12/ (Year: 2019).*

(Continued)

*Primary Examiner* — G. Steven Vanni
*Assistant Examiner* — Robert James Kallal
(74) *Attorney, Agent, or Firm* — Haynes and Boone, LLP

(57) ABSTRACT

The present disclosure provides systems and methods for controllable protein generation. According to some embodiments, the systems and methods leverage neural network models and techniques that have been developed for other fields, in particular, natural language processing (NLP). In some embodiments, the systems and methods use or employ models implemented with transformer architectures developed for language modeling and apply the same to generative modeling for protein engineering.

20 Claims, 16 Drawing Sheets

(56) References Cited

U.S. PATENT DOCUMENTS

| | | | |
|---|---|---|---|
| 2019/0286073 | A1 | 9/2019 | Asl et al. |
| 2019/0355270 | A1 | 11/2019 | Mccann et al. |
| 2019/0362020 | A1 | 11/2019 | Paulus et al. |
| 2020/0005765 | A1 | 1/2020 | Zhou et al. |
| 2020/0065651 | A1 | 2/2020 | Merity et al. |
| 2020/0084465 | A1 | 3/2020 | Zhou et al. |
| 2020/0089757 | A1 | 3/2020 | Machado et al. |
| 2020/0090033 | A1 | 3/2020 | Ramachandran et al. |
| 2020/0090034 | A1 | 3/2020 | Ramachandran et al. |
| 2020/0103911 | A1 | 4/2020 | Ma et al. |
| 2020/0104643 | A1 | 4/2020 | Hu et al. |
| 2020/0104699 | A1 | 4/2020 | Zhou et al. |
| 2020/0105272 | A1 | 4/2020 | Wu et al. |
| 2020/0117854 | A1 | 4/2020 | Lu et al. |
| 2020/0117861 | A1 | 4/2020 | Bradbury |
| 2020/0142917 | A1 | 5/2020 | Paulus |
| 2020/0175305 | A1 | 6/2020 | Trott et al. |
| 2020/0184020 | A1 | 6/2020 | Hashimoto et al. |
| 2020/0234113 | A1 | 7/2020 | Liu |
| 2020/0272940 | A1 | 8/2020 | Sun et al. |
| 2020/0285704 | A1 | 9/2020 | Rajani et al. |
| 2020/0285705 | A1 | 9/2020 | Zheng et al. |
| 2020/0285706 | A1 | 9/2020 | Singh et al. |
| 2020/0285993 | A1 | 9/2020 | Liu et al. |
| 2020/0302178 | A1 | 9/2020 | Gao et al. |
| 2020/0302236 | A1 | 9/2020 | Gao et al. |
| 2020/0334334 | A1 | 10/2020 | Keskar et al. |
| 2020/0364299 | A1 | 11/2020 | Niu et al. |
| 2020/0364542 | A1 | 11/2020 | Sun |
| 2020/0372116 | A1 | 11/2020 | Gao et al. |
| 2020/0372319 | A1 | 11/2020 | Sun et al. |
| 2020/0372339 | A1 | 11/2020 | Che et al. |
| 2020/0372341 | A1 | 11/2020 | Asai et al. |
| 2020/0380213 | A1 | 12/2020 | Mccann et al. |

OTHER PUBLICATIONS

Baclawski K. Ontology Summit 2018 Communique Contexts in Context. Applied Ontology 13(3): 1810-200. (Year: 2018).*

Jain A. NNTox: gene ontology-based protein toxicity prediction using neural network. Scientific Reports 9: 17923, pp. 1-10. (Year: 2019).*

Abadi et al.,TensorFlow: A system for large-scale machine learning, 2016, pp. 265-283, 12th USENIX Symposium on Operating Systems Design and Implementation.

Alley et al., Unified rational protein engineering with sequence-based deep representation learning, 2019, pp. 1315-1322, https://doi.org/10.1101/589333.

Ba et al., Layer Normalization, Jul. 21, 2016, 14 pages, https://arxiv.org/pdf/1607.06450.pdf.

Bairoch et al., Swiss-Prot: Juggling between evolution and stability, Mar. 2004, Briefings in bioinformatics, pp. 39-55.

Bairoch et al., The universal protein resource (uniprot), Nucleic acids research, 2005, pp. 154-159, Nucleic Acids Research, vol. 33.

Bengio et al., A Neural Probabilistic Language Model, pp. 1137-1155, 2003, Journal of Machine Learning Research 3.

Boeckmann, The Swiss-Prot protein knowledgebase and its supplement TrEMBL in 2003, Nucleic Acid Research, 2003, pp. 365-370, vol. 31., No. 1, Oxford University Press.

Devlin, Bert: Pre-training of Deep Bidirectional Transformers for Language Understanding, May 24, 2019, 16 pages, arXiv:1810.04805.

Child, R. et al., Generating long sequences with sparse transformers, Apr. 23, 2019, 10 pages, https://arxiv.org/pdf/1904.10509.pdf, arXiv:1904.10509.

Scott Federhen, The NCBI Taxonomy database, Dec. 2011, pp. 136-143, Nucleic Acids Research, vol. 40.

He et al., Deep Residual Learning for Image Recognition, Dec. 10, 2015, 12 pages, Proceedings of the IEEE Conference on Computer Vision and Pattern Recognition.

Henikoff et al., Amino Acid Substitution Matrices from Protein Blocks, Nov. 1992, pp. 10915-10919, Proc. Natl. Acad. Sci. USA, vol. 89, Proceedings of the National Academy of Sciences.

Vaswani et al., Attention Is All You Need, 2016, pp. 770-778, Proceedings of the IEEE conference on computer vision and pattern recognition, http://papers.nips.cc/paper/7181-attention-is-all-you-need.pdf.

Zellers et al., Defending Against Neural Fake News, Dec. 12, 2020, 21 pages, arXiv:1905.12616.

Shoeybi et al., Megatron-LM: Training Multi-Billion Parameter Language Models Using Model Parallelism, Mar. 13, 2020, 5 pages, arXiv:1909.08053.

Inan et al., Tying Word Vectors and Word Classifiers: A Loss Framework for Language Modeling, Mar. 11, 2017, 13 pages, ICLR 2017, arXiv:1611.01462.

Keskar et al., CTRL: A Conditional Transformer Language Model for Controllable Generation, Sep. 20, 2019, 18 pages, arXiv:1909.05858.

Kingma et al., Adam: A Method for Stochastic Optimization, Jan. 30, 2017, 15 pages, ICLR 2015, arXiv:1412.6980.

Leinonen et al., UniProt archive, Bioinformatics Applications Note, Sep. 17, 2003, pp. 3236-3237, Bioinformatics, vol. 20 No. 17.

McCann et al., Learned in Translation: Contextualized Word Vectors, 2017, pp. 6294-6305, Advances in Neural Information Processing Systems.

Nair et al., Rectified Linear Units Improve Restricted Boltzmann Machines, 2010, pp. 807-814, Proceedings of the 27th International Conference on Machine Learning, ICML-10.

Peters et al., Deep Contextualized Word Representations, Mar. 22, 2018, 15 pages, arXiv: 1802.05365.

Press et al., Using the Output Embedding to Improve Language Models, Feb. 21, 2017, 7 pages, arXiv: 1608.05859.

Radford et al., Language Models are Unsupervised Multitask Learners, 2019, https://d4mucfpksywv.cloudfront.net/better-language-models/language_models_are_unsupervised_multitask_learners.pdf.

Rae et al., Compressive Transformers for Long-Range Sequence Modelling, Nov. 13, 2019, arXiv:1911.05507.

Rao et al., Evaluation Protein Transfer Learning with TAPE, Jun. 19, 2019, pp. 9686-9698, Advances in Neural Information Processing Systems.

Rives et al., Biological Structure and Function Emerge from Scaling Unsupervised Learning to 250 Million Protein Sequences, 2019, pp. 622-803, bioRxiv.

* cited by examiner

SYSTEMS AND METHODS FOR LANGUAGE MODELING OF PROTEIN ENGINEERING

CROSS REFERENCES

This application is a nonprovisional application of and claims priority under 35 U.S.C. 119 to commonly-owned U.S. provisional application No. 62/971,119, filed Feb. 6, 2020.

This application is related to commonly-owned U.S. nonprovisional application Ser. No. 17/001,045 and Ser. No. 17/001,090, both filed on the same day.

All of the aforementioned applications are hereby expressly incorporated herein by reference in their entirety.

TECHNICAL FIELD

The present disclosure relates generally to machine learning models and neural networks, and more specifically, to conditional language modeling for protein generation.

BACKGROUND

Generating proteins with desired properties is one of the most complex and impactful problems in biology. A protein is encoded by a specific raw amino acid sequence, and during synthesis, this chain of amino acids folds in ways that exhibit a local (e.g., secondary) and a global (e.g., tertiary) structure. These structural properties then directly determine a unique function of the synthesized protein, e.g., to serve as part of a vaccine to certain virus, a catalyst, etc. Synthesizing proteins that are actually functional is one of the goals for protein engineering. Unfortunately, obtaining three-dimensional structural information for proteins is expensive and time consuming.

Traditionally, protein engineering, such as directed evolution, largely relies on heuristics and random mutations to select initial sequences for rounds of evolution in order to generate new proteins. However, as the protein sequence data grows exponentially as compared to its structural data, heuristics-based protein engineering renders very limited success in the past.

Therefore, there is a need for efficient protein engineering.

Figure 1:
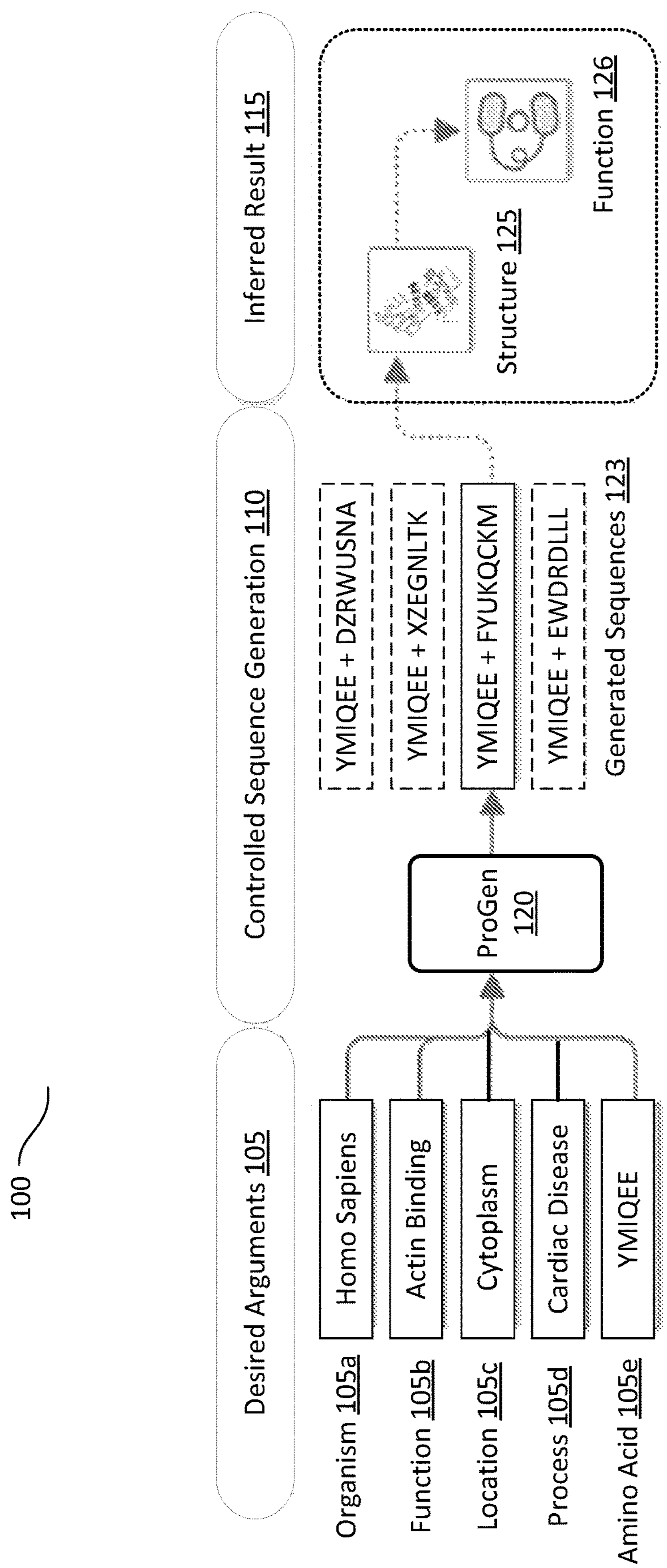
FIG. 1 provides a block diagram illustrating an overview of controlled protein generation using a language model-based protein generation model (hereinafter "ProGen"), according to an embodiment.

In the figures, elements having the same designations have the same or similar functions.

DETAILED DESCRIPTION

Artificial intelligence, implemented with neural networks and deep learning models, has demonstrated great promise as a technique for automatically analyzing real-world information with human-like accuracy. In general, such neural network and deep learning models receive input information and make predictions based on the same. Whereas other approaches to analyzing real-world information may involve hard-coded processes, statistical analysis, and/or the like, neural networks learn to make predictions gradually, by a process of trial and error, using a machine learning process. A given neural network model may be trained using a large number of training examples, proceeding iteratively until the neural network model begins to consistently make similar inferences from the training examples that a human might make. Neural network models have been shown to outperform and/or have the potential to outperform other computing techniques in a number of applications.

A potential application for artificial intelligence is in the field of protein engineering. Generating proteins with desired properties is one of the most complex yet impactful problems in biology and science. Proteins are the workhorse for almost any fundamental process in life—from oxygen transport to immune system response. Protein engineering research has grown over the past 50 years and yielded remarkable outcomes including the development of new enzymes, therapies, and sensors. However, leading experimental techniques for protein engineering rely on structural annotations that accompany a small subset of sequenced protein. Unfortunately, obtaining structural annotations for raw sequences of amino acids that form a functional protein is expensive and time consuming.

Recent research has begun to capitalize on the much larger set of raw protein sequences by adapting state-of-the-art representation learning techniques from natural language processing to classification of protein properties. However, these methods have yet to capitalize on the large amount of non-structural annotations available for these sequences such as host organism, biological process, cellular component, and molecular function. In particular, there has been no attempt to adapt learning techniques from natural language processing to generate new proteins. In this regard, protein synthesis largely relies on the traditional heuristics-based or random mutation methods, which yields limited success in producing a functional protein.

According to some embodiments described herein, in view of limited success on traditional protein engineering methods, the present disclosure provides systems and methods for controllable protein generation. According to some embodiments, the systems and methods leverage neural network models and techniques that have been developed for other fields, in particular, natural language processing (NLP). In some embodiments, the systems and methods use or employ models implemented with transformer architectures developed for language modeling and apply the same to generative modeling for protein engineering.

As used herein, the term "protein generation" refers to generating a data sequence of amino acids that may be potentially used for protein synthesis in a laboratory.

FIG. 1 provides a block diagram illustrating an overview 100 of controlled protein generation using a language model-based protein generation model (hereinafter "ProGen"), according to an embodiment. As shown in FIG. 1, protein generation 120 receives an input of desired/target arguments/properties 105 of a protein, such as the organism 105*a* ("*Homo sapiens*"), function 105*b* ("action binding"), location 105*c* ("cytoplasm"), process 105*d* ("cardiac disease"), and/or the like, and amino acids 105*e* ("YMIQEE," etc). Specifically, protein generation model 120 encodes the target protein properties into a set of conditional tags and combine the set of conditional tags with a context sequence of amino acids as an input vector. Protein generation model 120 then uses a language model for controlled sequence generation 110 from the input vector. Specifically, protein generation model 120 generates a next-token prediction distribution over the input amino acids. The constituent amino acids can then be sequentially sampled from the context sequence of amino acids based on the next-token prediction distribution to form an output protein sequence 123.

The inferred results 115 from the generated protein sequence 123 may then be analyzed, e.g., whether the generated protein sequence 123 achieve the target structure 125 and the target functions 126.

According to some embodiments, the systems of the present disclosure—including the protein generation model protein generation model 120—can be implemented in one or more computing devices.

Figure 2:
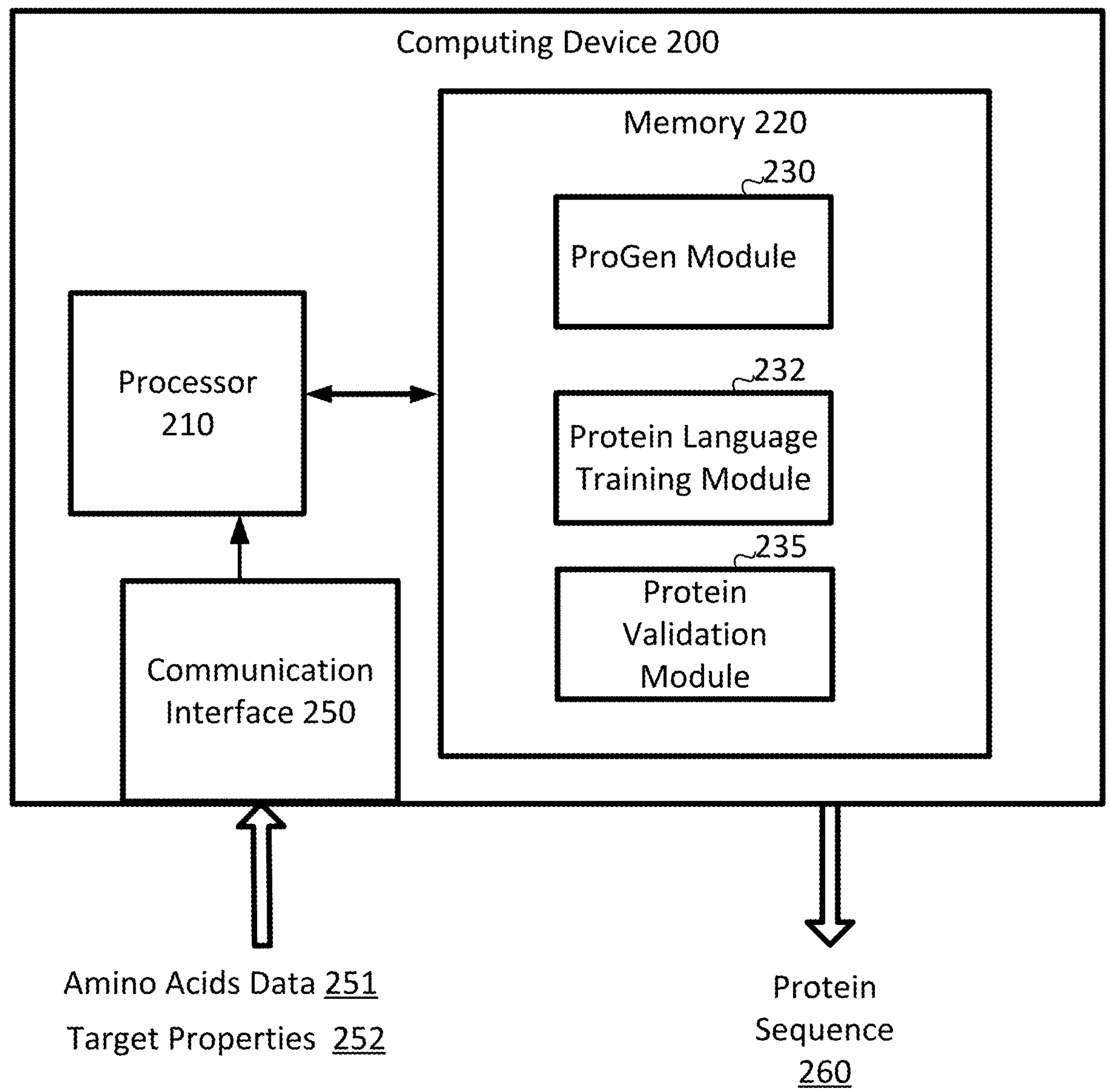
FIG. 2 is a simplified diagram of a computing device according to some embodiments.

FIG. 2 is a simplified diagram of a computing device 200 according to some embodiments. As shown in FIG. 2, computing device 200 includes a processor 210 coupled to memory 220. Operation of computing device 200 is controlled by processor 210. And although computing device 200 is shown with only one processor 210, it is understood that processor 210 may be representative of one or more central processing units, multi-core processors, microprocessors, microcontrollers, digital signal processors, field programmable gate arrays (FPGAs), application specific integrated circuits (ASICs), graphics processing units (GPUs) and/or the like in computing device 200. Computing device 200 may be implemented as a stand-alone subsystem, as a board added to a computing device, and/or as a virtual machine.

Memory 220 may be used to store software executed by computing device 200 and/or one or more data structures used during operation of computing device 200. Memory 220 may include one or more types of machine readable media. Some common forms of machine readable media may include floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

Processor 210 and/or memory 220 may be arranged in any suitable physical arrangement. In some embodiments, processor 210 and/or memory 220 may be implemented on a same board, in a same package (e.g., system-in-package), on a same chip (e.g., system-on-chip), and/or the like. In some embodiments, processor 210 and/or memory 220 may include distributed, virtualized, and/or containerized computing resources. Consistent with such embodiments, processor 210 and/or memory 220 may be located in one or more data centers and/or cloud computing facilities.

As shown, memory 220 includes a protein generation module 230 that may be used, in some examples, for generative modeling for protein engineering. In some examples, protein generation module 230 may be implemented using hardware, software, and/or a combination of hardware and software. In some examples, memory 220 may include non-transitory, tangible, machine readable media that includes executable code that when run by one or more processors (e.g., processor 210) may cause the one or more processors to perform the methods described in further detail herein.

As shown, computing device 200 receives an input via a communication interface 250, which is provided to protein generation module 230. This input may comprise data for one or more sequences of amino acids 251 for generating proteins, and a set of target protein properties 252, such as but not limited to properties 105*a-d* shown in FIG. 1. Protein generation module 230 may generate output 260, which may comprise data for a protein sequence by module 230.

According to some embodiments, protein generation module 230 may implement and/or emulate one or more neural network systems and models, and corresponding methods, for generative modeling for protein engineering. In some embodiments, protein generation module 230 may comprise, incorporate, or employ a neural network model that has been developed for natural language processing (NLP). For example, this neural network language model can be a transformer-based architecture, such as the Open AI GPT-2. Large transformer architectures represent the state-of-the-art in unconditional language modeling and demonstrate impressive text generation capabilities after training on vast amounts of unsupervised text. Large transformer architectures have been trained for language generation by conditioning on "control codes" that represent specific properties of the text readily extracted at scale, e.g. domain, style, and even associated URL. This is described in more detail in Keskar et al., "A conditional transformer language model for controllable generation," arXiv preprint arXiv: 1909.05858, 2019, which is incorporated by reference herein. In some embodiments, the systems and methods adapt the perspective and techniques of Keskar et al. (2019) to protein engineering by training a conditional transformer language model for proteins (amino acid sequences) conditioned on a set of protein properties cast as control codes. Protein engineering may require a finer-grained, larger, and more complex set of control codes. Rather than having only a few control codes associated with a document (in language modeling), in protein engineering a single protein is paired with dozens of control codes and the protein itself contains relatively few unique tokens that are not control codes.

Memory 220 further includes a protein language training module 232. According to some embodiments, protein engineering can be posed as an unsupervised sequence generation problem in order to leverage the exponentially growing set of proteins that lack costly, structural annotations. One challenge to obtain training data for protein generation is the vast volume of protein sequences that lack structural annotations. The protein language training module 232 provides a training mechanism for using protein language (as opposed to human languages) to train a language model for protein engineering. The protein language training module 232 obtains protein sequences and associated tags available, and creates training protein data samples that are suitable for a language model. For example, protein sequence data along with taxonomic and keyword tags can be used to train protein generation module 230. In this way, the protein generation module 230 can trained by as a language model in a similar manner that the language model can be trained with human language samples using the protein language training samples provided by the protein language training module 232.

For example, protein generation module 230 can be a 1.2B-parameter neural network language model is trained on a dataset of ~270M protein sequences together with conditioning tags from the protein generation module 230. The protein generation module 230 encodes a variety of different kinds of annotation such as taxonomic, functional, and structural information into the conditional tags. By conditioning on these tags, protein generation module 230 provides a new method for protein generation that can be tailored for desired properties. In some embodiments, protein generation module 230 can be a powerful language model, achieving comparable performance to similarly sized models for human languages. This performance improves in settings with larger amino acid contexts and when protein generation model is provided a larger number of conditioning tags, which highlights its potential for applications such as hot-spot generation. The protein generation model also performs well when used to model unseen protein families. Furthermore, in some embodiments, protein generation module 230 can be fine-tuned for those unseen families as an alternative to training from random initialization, which may make it even more effective.

Memory 229 further includes a protein validation module 235. One goal of protein engineering is to generate a new protein that is both structural and functional relevant. The protein validation module 235 validates the relevancy of the generated protein sequence from the protein generation module 230. For structural relevancy, the protein validation module 235 evaluates three levels of structures: primary sequence similarity, secondary structure accuracy and conformational energy analysis of the engineered protein sequence 260. For functional accuracy of the engineered protein 260, the protein validation module 235 adopts zero-shot selection among variants of engineered proteins with the lowest perplexity values to achieve high fitness proteins.

The protein validation module 235 may further use sequence similarity, secondary structure accuracy, and conformational energy to assess how well the proteins generated by the protein generation model satisfy desired structural and functional properties specified by the conditioning tags. Proteins generated from the protein generation model appear of higher quality according to metrics that describe higher level structure. This indicates that amino acid substitutions marked as errors according to lower-level metrics are likely to be acceptable substitutions that conserve structure and function at the more relevant higher levels of evaluation. This suggests that the protein generation model has learned to generate within the constraints of natural, structural invariances to substitutions in amino acid sequences. Conformational energy analysis reveals that the protein generation model generates proteins that are near the energy levels of native proteins, providing further evidence that they fulfill the desired functional properties.

Figure 3:
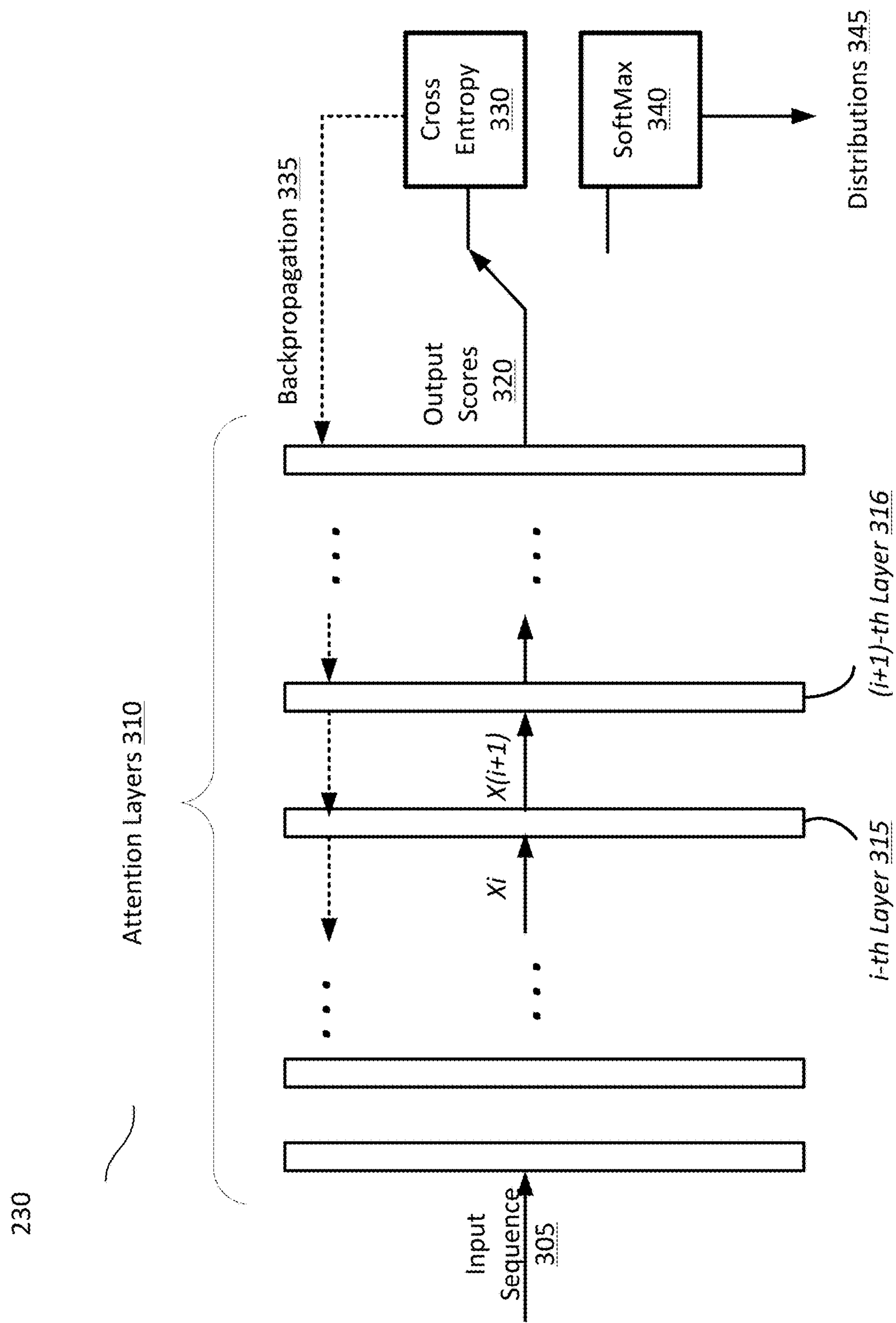
FIG. 3 provides a block diagram illustrating an example structure of the protein generation module described in FIG. 2, according to some embodiments described herein.

FIG. 3 provides a block diagram illustrating an example structure of the protein generation module 230 described in FIG. 2, according to some embodiments described herein. In some embodiments, the protein generation module 230 includes a number of attention layers 310, which receives an input sequence 305 at an input layer, and outputs a set of output scores 320. Specifically, the input sequence 305 includes a first portion of a data sequence of amino acids that constitutes a protein, denoted by $a=(a_1, a_2, \ldots a_{na})$, where $n_a$ denotes the desired length of the protein. The input sequence 305 also includes a second portion of a set of conditioning tags representing target protein properties, through which generation of amino acid sequences can be controlled. The set of conditional tags is denoted by $c=(c_1, \ldots, c_{nc})$, where $n_c$ denotes the total number of conditional tags, and the input sequence 305 can then be expressed by $x=[c; a]$, the sequence formed by prepending a conditioning tag sequence c to an amino acid sequence a. p(x) is then the probability distribution over such combined sequences of length $n=n_a+n_c$, which can be factorized using the chain rule of probability:

$$p(x) = \prod_{i=1}^{n} p(x_i \mid x_{<i})$$

In this way, conditional protein generation can be reformulated as next-token prediction in natural language processing, where a token $x_i$ can either be an amino acid or a conditioning tag from x.

The attention layers 310 may be a variant of the Transformer that learns the conditional distributions over amino acids and conditioning tags. Further details of the Transformer can be found in Vaswani et al., Attention is All You Need, in proceedings of NIPS, 2017, which is hereby expressly incorporated by reference herein in its entirety. The input sequence x containing n tokens is embedded as a sequence of n corresponding vectors in $R^d$. Each vector is the sum of a learned token embedding and a sinusoidal positional embedding as in the original Transformer architecture. This sequence of vectors is stacked into a matrix $x_0 \in R^{n \times d}$ so that it can be processed by l attention layers. Specifically, the ith layer 315 receives an input of $X_i$ from the preceding layer and then generates an output of $X_{i+1}$ which is fed to the next attention layer 316.

Figure 4:
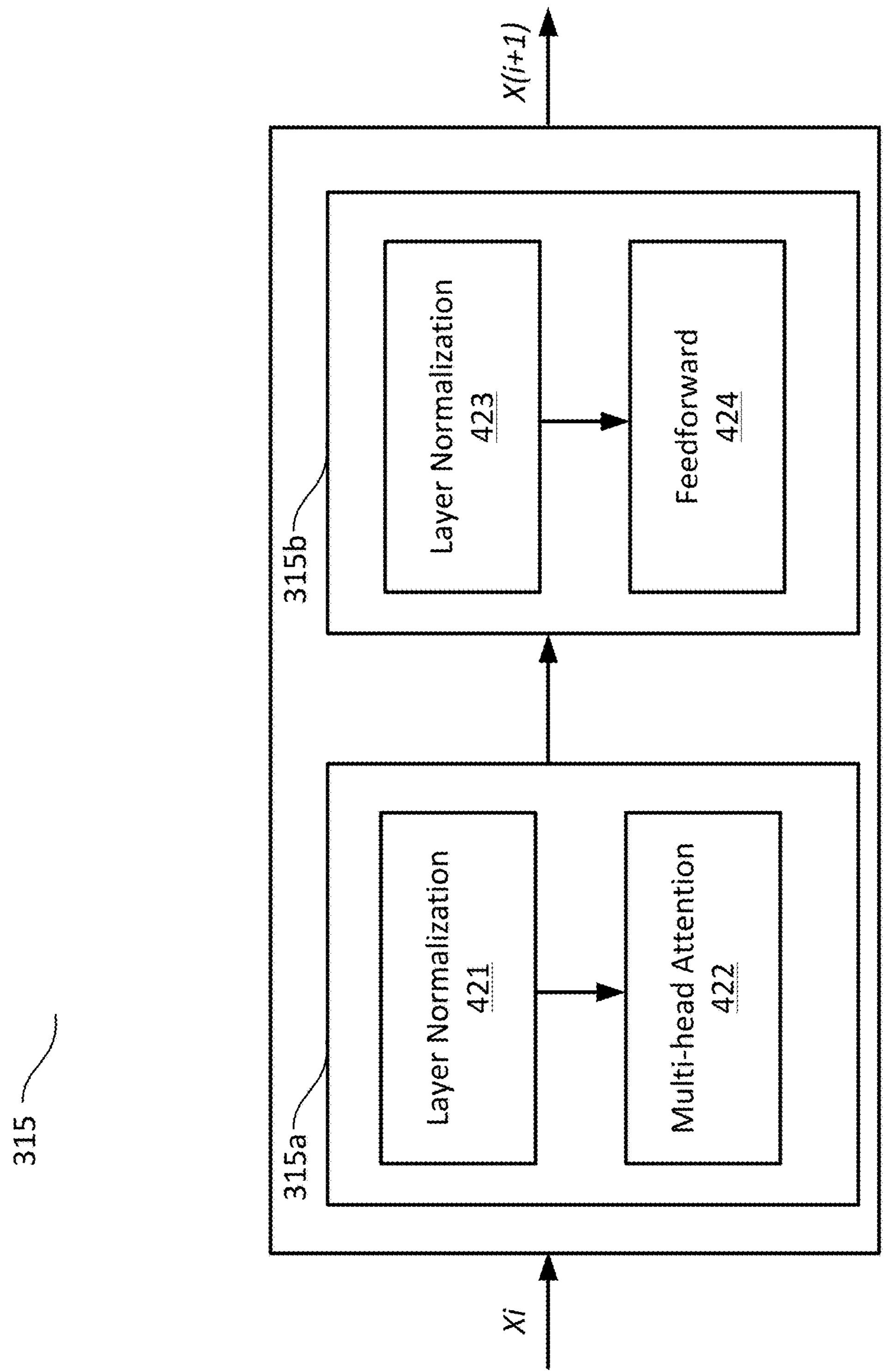
FIG. 4 provides a block diagram illustrating an example structure of each attention layer in FIG. 3, according to embodiments described herein.

FIG. 4 provides a block diagram illustrating an example structure of each attention layer 315 or 316 in FIG. 3, according to embodiments described herein. The ith layer 315 consists of two blocks 315*a-b*, each of which preserves the model dimension d. The first block 315*a* includes a layer normalization module 421 and a multi-head attention module 422. The layer normalization module 421 can be similar to the layer normalization discussed in Child et al., Generating long sequences with sparse transformers, arXiv preprint arXiv: 1904.10509, 2019, which is hereby expressly incorporated by reference herein in its entirety. The multi-head attention module has k heads that use a causal mask to preclude attending to future tokens, defined by:

$$\text{MultiHead}(X, k) = [h_1; \ldots ; h_k]W_o,$$

$$\text{where } h_j = \text{Attention}(XW_j^1, XW_j^2, XW_j^3),$$

$$\text{and Attention}(X, Y, Z) = \text{softmax}\left(\frac{\text{mask}(XY^T)}{\sqrt{d}}\right)Z,$$

Thus, the first block 315*a* can be operated as follows:

$$\overline{X}_i = \text{LayerNorm}(X_i),$$

$$H_i = \text{MultiHead}(\overline{X}_i) + \overline{X}_i$$

where $H_i$ is the output of the first block 315*a.*

The second block 315*b* consists of a layer normalization module 423 and a feedforward network 424. The feedforward network 424 includes ReLU activation that projects inputs to an inner dimension f, with parameters $U \in R^{f \times d}$: FF(X)=max(0, XU)V. Thus, the second block 315*b* can be operated as follows:

$$\overline{H}_i = \text{LayerNorm}(H_i),$$

$$X_{i+1} = FF(\overline{H}_i) + \overline{H}_i.$$

With reference to FIG. 3, at the lth (last) layer of the attention layers 310, scores 320 are then computed from the output of the last layer:

$$\text{Scores}(X_0) = \text{LayerNorm}(X_l)W_{vocab}$$

where $W_{vocab}$ denotes a weight matrix having a dimension of the same size as the number of tokens in the token vocabulary. The $W_{vocab}$ matrix transforms the normalization layer output to a score per token.

During generation, the output scores 320 corresponding to the final token are then normalized with a softmax module 340, yielding a distribution for sampling a new token. During training, the output scores 320 are the inputs of a cross-entropy module 330. Specifically, the neural network of the attention layers 310 with parameters θ can then be trained to minimize the negative log-likelihood over a training dataset $D=[x^1, x^2, \ldots x^{|D|}]$:

$$\mathcal{L}(D) = -\sum_{k=1}^{|D|}\sum_{i=1}^{n}\log p_\theta(x_i^k \mid x_{<i}^k)$$

Note that p(a|c), the distribution over proteins conditioned on their corresponding conditioning tags, is just one of the many conditional distributions that can be re-covered from a model that learns p(x). Thus, during generation, a new protein ã of length m a with desired properties encoded by a conditioning tag sequence c̃ of length $m_c$ can then be generated by sequentially sampling its constituent symbols: $p_\theta(a_0|\tilde{c})$, $p_\theta(a_1|\tilde{a}_0, \tilde{c})$, $p_\theta(a_p|\tilde{a}_{<p}, \tilde{c})$.

Figure 5:
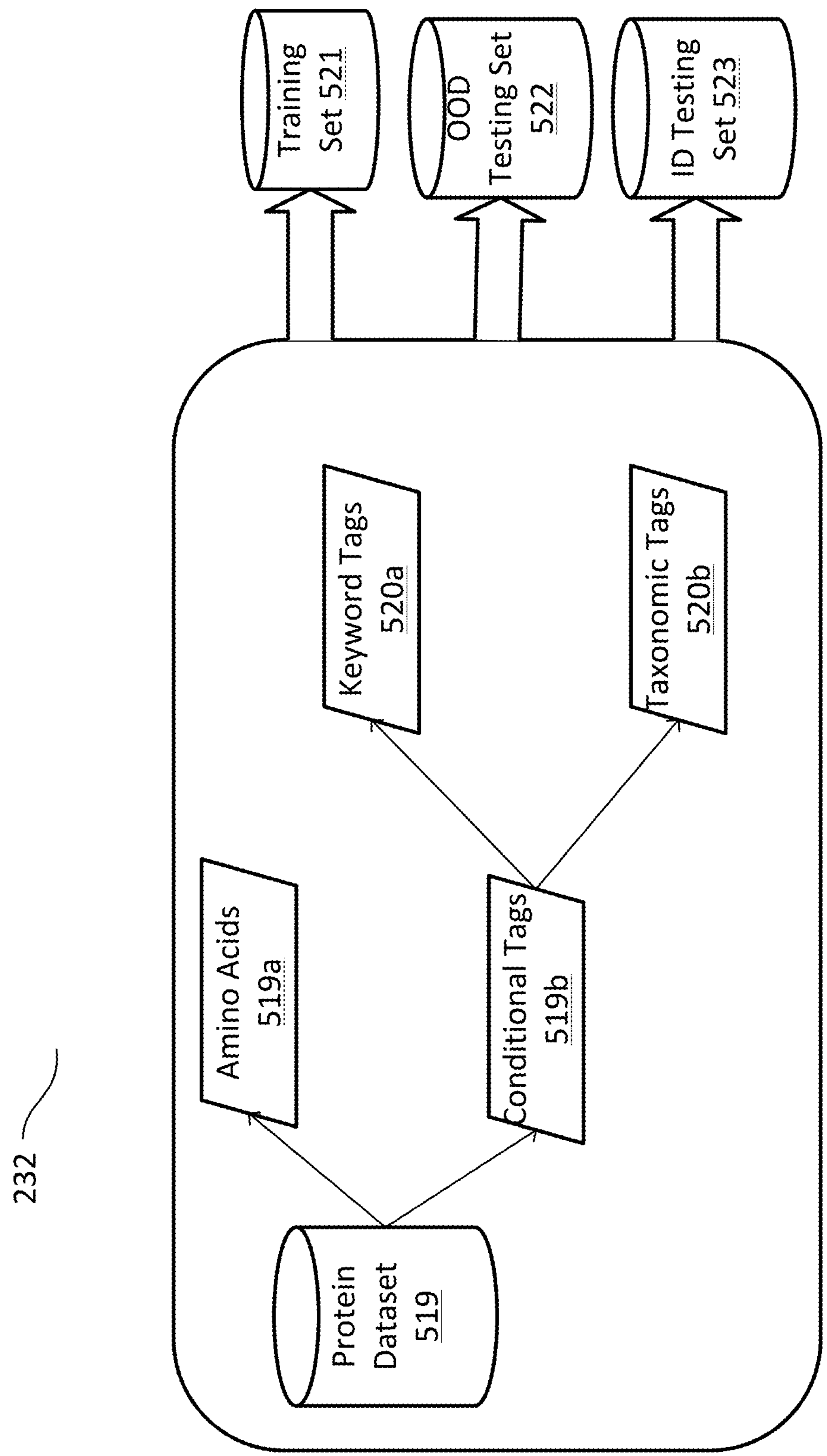
FIG. 5 provides an example block diagram illustrating preparing training data by the protein language training module for the protein generation module in FIGS. 2-3, according to some embodiments described herein.

FIG. 5 provides an example block diagram illustrating preparing training data by the protein language training module 232 for the protein generation module 230 in FIGS. 2-3, according to some embodiments described herein. Specifically, the protein language training module 232 may obtain protein sequences and associated tags available from a protein dataset 519. For example, the protein dataset 519 may be any combination of the available protein databases such as but not limited to Uniparc (see Leinonen et al., Uniprot archive, Bioinformatics, 20(17):3236-3237, 2004), UniprotKB (see Bairoch et al., The universal protein resource (uniprot). Nucleic acids research, 33(suppl 1):D154-D159, 2005), SWISSPROT (see Bairoch et al., Swiss-prot: juggling between evolution and stability. Briefings in bioinformatics, 5(1):39-55, 2004), TrEMBL (see Boeckmann et al., The swiss-port protein knowledgebase and its supplement trembl in 2003. Nucleic acids research, 31(1):365-370, 2003), Pfam (see Bateman et al., The pfam protein families database. Nucleic acids research, 32(suppl 1):D138-D141, 2004), and NCBI taxonomic information (see Federhen, The NCBI taxonomy database. Nucleic acids research, 40(D1):D136-D143, 2012). All of the aforementioned publications are hereby expressly incorporated by reference herein in their entirety.

In some embodiments, the aggregated dataset 519 may contain over 281M proteins, which can be the most comprehensive, non-redundant, annotated database of proteins used to train a machine learning model. The protein data from the protein dataset 519 contains amino acids 519*a*, which uses a vocabulary according to the 25 amino acids designations in IUPAC (see Pettit et al., The iupac stability constants database. Chemistry international, 2006). The conditioning tags 519*b* associated with the protein data are divided into 2 categories: (1) keyword tags 520*a* and (2) taxonomic tags 520*b*. Following the definitions laid out in the UniprotKB controlled, and hierarchical vocabulary of keywords (many of which are derived from Gene Ontology (GO) terms), the conditioning keyword tags 520*a* included 1100 terms ranging from cellular component, biological process, and molecular function terms. The taxonomic tags 520*b* include 100 k terms from the NCBI taxonomy across the eight standard taxonomic ranks. The aggregated dataset can then be split into a training set 521 of size 280M, a held-out protein family test set (OOD-test) 522 of size 100 k, and a randomly sampled test set (ID-test) 523 of size 1M.

In some embodiments, OOD-test set 522 comprises 20 protein families, as defined in Pfam, that were excluded from the training dataset 521. As further illustrated in Table 1, performance on OOD-test measures ability to model samples from unseen protein families, whereas performance on ID-test measures ability to model samples from a wider range of protein families that more closely match the distribution of the training set.

Figure 6:
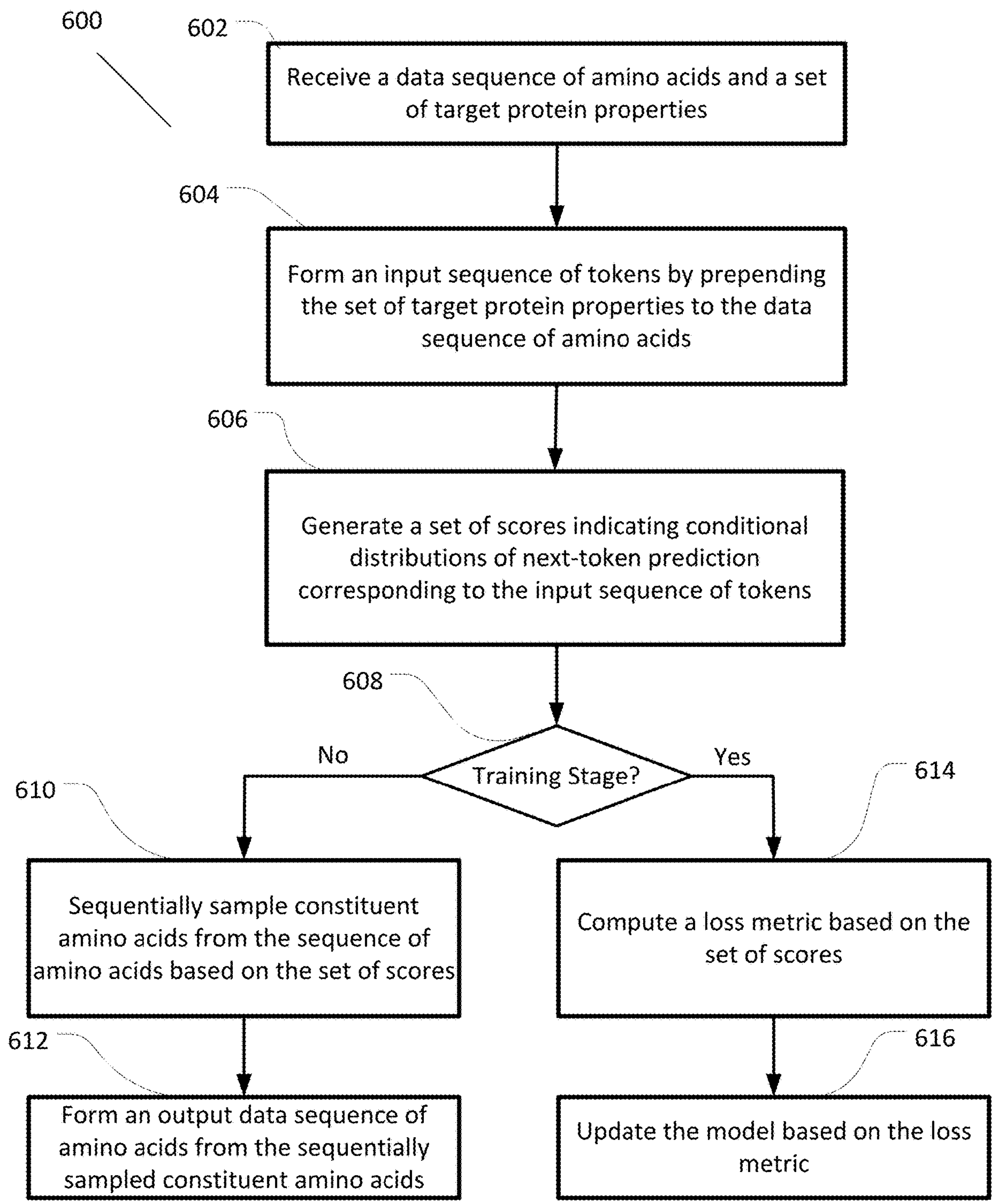
FIG. 6 is a simplified diagram of a method for conditional language modeling for protein generation, according to some embodiments.

FIG. 6 is a simplified diagram of a method 600 for conditional language modeling for protein generation, according to some embodiments. One or more of the processes of method 600 may be implemented, at least in part, in the form of executable code stored on non-transitory, tangible, machine-readable media that when run by one or more processors may cause the one or more processors to perform one or more of the processes. In some embodiments, method 600 corresponds to the operation of protein generation module 120 in FIG. 1 or protein generation module 230 in FIG. 2 to perform conditional language modeling for protein generation.

At process 602, the protein generation module (e.g., 120 or 230) receives a data sequence of amino acids and a set of target protein properties. For example, data relating to amino acids 519*a* and the conditional tags 519*b* representing protein properties can be received from multiple protein databases discussed in relation to FIG. 5. In some embodiments, the target protein properties may be artificially defined for a target new protein.

At process 604, the module forms an input sequence of tokens by prepending the set of target protein properties to the data sequence of amino acids, e.g., the input sequence 305 as discussed in relation to FIG. 3.

At process 606, a set of scores indicating conditional distributions of next-token prediction corresponding to the input sequence of tokens is generated. For example, a unidirectional Transformer architecture comprising multiple attention layers 310 may be used to generate the output scores 320 as described in relation to FIG. 3.

The module then determines whether it is at a training stage or a generation stage at process 608. If the module is at training stage, method 600 proceeds to process 614, at which the module computes a loss metric based on the set of scores over an input training dataset, e.g., a negative log-likelihood function £(D) as discussed in relation to FIG. 3. At process 616, the module is updated based on the loss metric, e.g., via backpropagation 335 in FIG. 3.

If the module is at generation stage (e.g., not at training stage at process 608), method 600 proceeds to process 610, at which constituent amino acids from the data sequence of amino acids based on the set of scores. Specifically, the module generates proteins one amino acid at a time. For instance, at one step of generation, the module takes a context sequence of amino acids as input and outputs a probability distribution over amino acids. The module determines one amino acid based on the probability distribution (e.g., by sampling over the distribution) and then the context sequence is updated with the sampled amino acid. This process repeats until a protein sequence of desired length has been generated.

At process 612, an output data sequence of amino acids is formed from the sequentially sampled constituent amino acids. For example, the output data sequence of amino acids may be provided to a protein synthesis facility such as a bio-chemical laboratory for synthesizing the protein.

Figure 7:
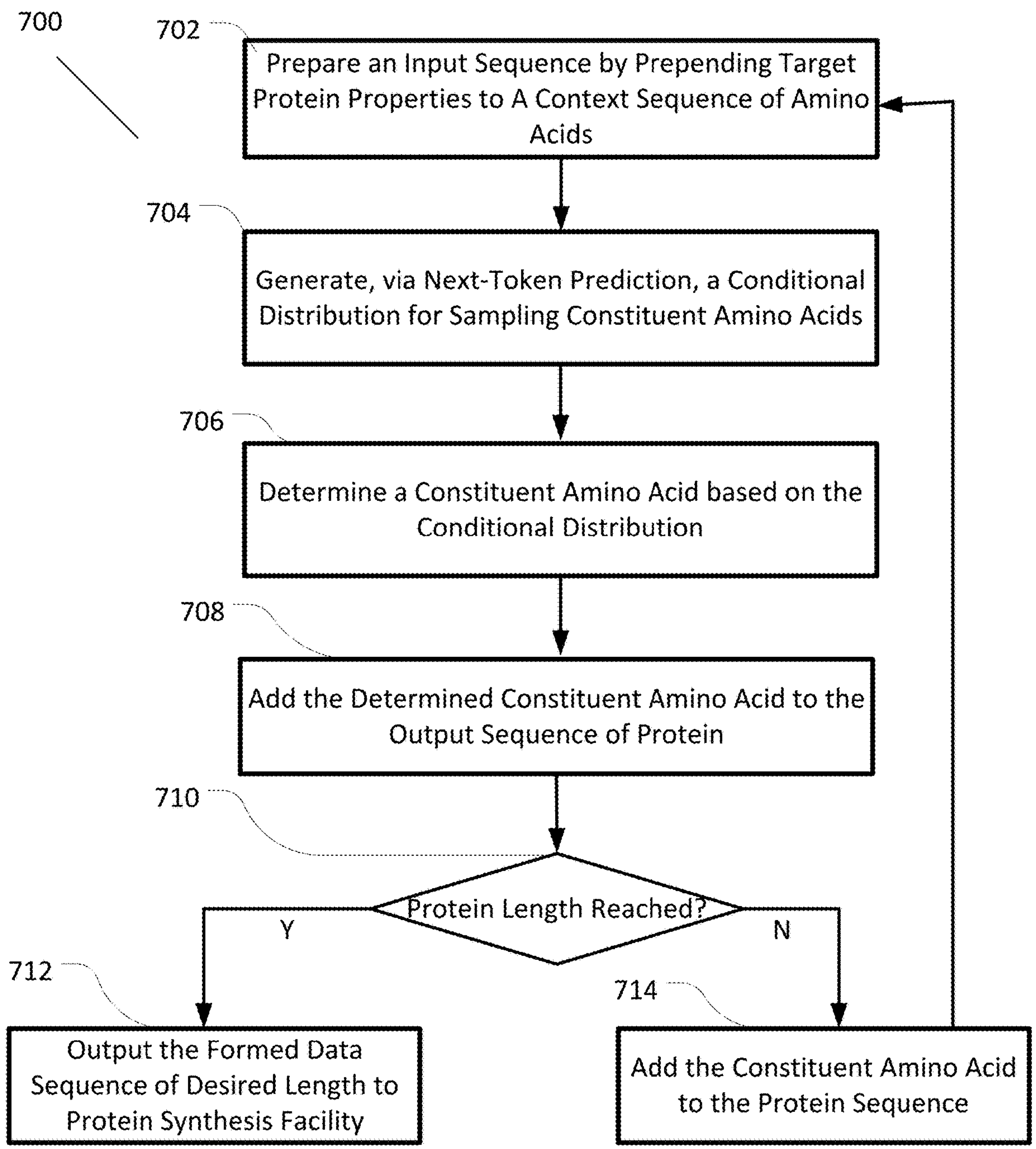
FIG. 7 is a simplified diagram of a method for sequentially generating an output data sequence of amino acids using a language model, according to some embodiments.

FIG. 7 is a simplified diagram of a method 700 for sequentially generating an output data sequence of amino acids using a language model, according to some embodiments. One or more of the processes of method 700 may be implemented, at least in part, in the form of executable code stored on non-transitory, tangible, machine-readable media that when run by one or more processors may cause the one or more processors to perform one or more of the processes. In some embodiments, method 700 corresponds to the operation of protein generation module 120 in FIG. 1 or protein generation module 230 in FIG. 2 to perform conditional language modeling for protein generation.

Method 700 starts at a generation stage of the protein generation module, e.g., method 700 may proceed from process 610 in FIG. 6. At process 702, an input sequence can be prepared by prepending the target protein properties to a context sequence of amino acids, e.g., x=[c; a]. At process 704, a conditional distribution for sampling constituent amino acids can be generated via next-token prediction by the language model. For example, the conditional probability of the next constituent amino acids given the current context sequence of amino acids may be generated. At process 706, the next constituent amino acids may be determined, from the context sequence of amino acids based on the conditional distribution. At process 708, the determined constituent amino acid is then added to the output data sequence of amino acids for generating the output protein.

At process 710, if the desired protein length has been reached, method 700 proceeds to process 712, where the formed data sequence of desired length is output to a protein synthesis facility (e.g., a laboratory setting, etc.) for protein generation. Otherwise, if the current output sequence of amino acids has not reached the desired protein length, the method 700 proceeds to process 714, at which the constituent amino acids is added to the protein sequence.

In some embodiments, different combinations of data sequences of amino acids are generated by top-k sampling with a repetition penalty. The top-k sampling may be applied in a similar way as discussed in Radford et al., Generating long sequences with sparse transformers. arXiv preprint arXiv: 1904.10509, 2019, which is hereby expressly incorporated by reference herein in its entirety. The repetition penalty reduces the probability that the same amino acid previously determined within four tokens prior to the current token is determined again. Instead, top-k sampling draws the next token from the k most probable tokens in the distribution output from the language model. For example, results for top-k values of k=1 and k=3 with repetition penalties of 0 and 1.2 may be used for determining the next amino acid.

Figure 8:
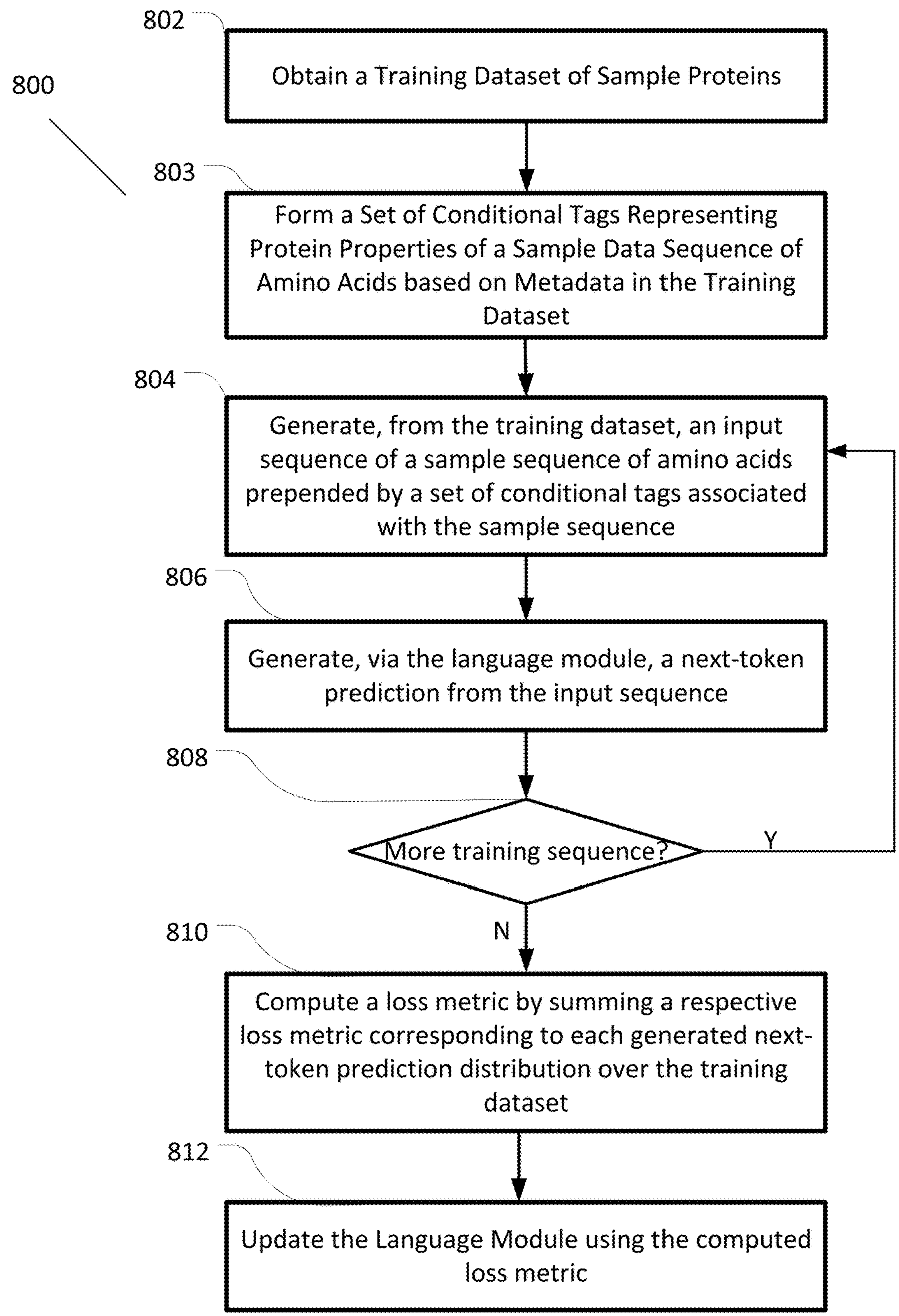
FIG. 8 is a simplified diagram of a method for training a language model using protein data, according to some embodiments.

FIG. 8 is a simplified diagram of a method 800 for training a language model using protein data, according to some embodiments. One or more of the processes of method 800 may be implemented, at least in part, in the form of executable code stored on non-transitory, tangible, machine-readable media that when run by one or more processors may cause the one or more processors to perform one or more of the processes. In some embodiments, method 800 corresponds to the training of protein generation module 120 in FIG. 1 or protein language training module 232 in FIG. 2 to prepare training data based on protein data that are suitable for training a language model.

At process 802, a training dataset is obtained, e.g., from protein database 519 shown in FIG. 5. For example, the training data may be obtained from protein database such as Uniparc, UniprotKB, SWISS-PROT, NCBI, and/or the like. The aggregated dataset may contain over the data sequence of amino acids and the associated protein properties for over 280M proteins.

At process 803, a set of conditional tags representing protein properties of a sample data sequence of amino acids may be formed based on metadata in the training dataset. For example, the conditional tags 519*b* may be further divided into keyword tags 520*a* and taxonomic tags 520*b* as discussed in relation to FIG. 5.

At process 804, an input sequence is generated by prepending the set of conditional tags associate with the sample sequence to a sample data sequence of amino acids. In some embodiments, for a given sequence, there can be multiple versions of conditional tags across databases, each with their own associated conditioning tags. In training, the conditional tags may be randomly sampled but a bias toward SWISSPROT tags may be applied as they are manually verified.

In some embodiments, a dropout may be applied to the conditioning tags themselves at a rate of 0.4. In some embodiments, a sample data sequence of amino acids with the data sequence alone without conditioning tags is fed to the language model so that the language model can be used to complete proteins using only sequence data even when no protein properties are known.

In some embodiments, the input sequences are truncated to a maximum length of 512. Sequences of length less than 512 may be padded, but no loss was backpropagated through the network for padding tokens.

At process 806, a next-token prediction is generated by the language model from the generated input sequence. For example, the resulting language model has dimension d=1028, inner dimension f=512, 36 layers, and 8 heads per layer. Dropout may be applied with a probability of 0.1 that follows the residual connections in each layer. Token embeddings may be tied with the embeddings of the final output layer. For another example, the language model may be implemented in TensorFlow, as discussed in further detail in Abadi et al., Tensorflow: A system for large-scale machine learning, in 12th Symposium on Operating Systems Design and Implementation, pp. 265-283, 2016, which is hereby expressly incorporated by reference herein in its entirety.

At process 808, if there are more training sequences, method 800 proceeds to process 804 and repeats processes 804-806. If no more training sequence is available, method 800 proceeds to process 810, at which a loss metric is computed by summing a respective loss metric corresponding to each generated next-token prediction distribution over the training dataset. For example, the loss metric may be computed using the negative log-likelihood over the training dataset, as discussed in relation to FIG. 4.

At process 812, the language model may be updated using the computed loss metric. For example, the language model may be trained with a global batch size of 64 distributed across 256 cores of a Cloud TPU v3 Pod for 1M iterations. As an example, training may take approximately two weeks with a linear warmup from 0 to 1e-2 over 40 k steps. Gradient norms were clipped to 0.25.

Figure 9:
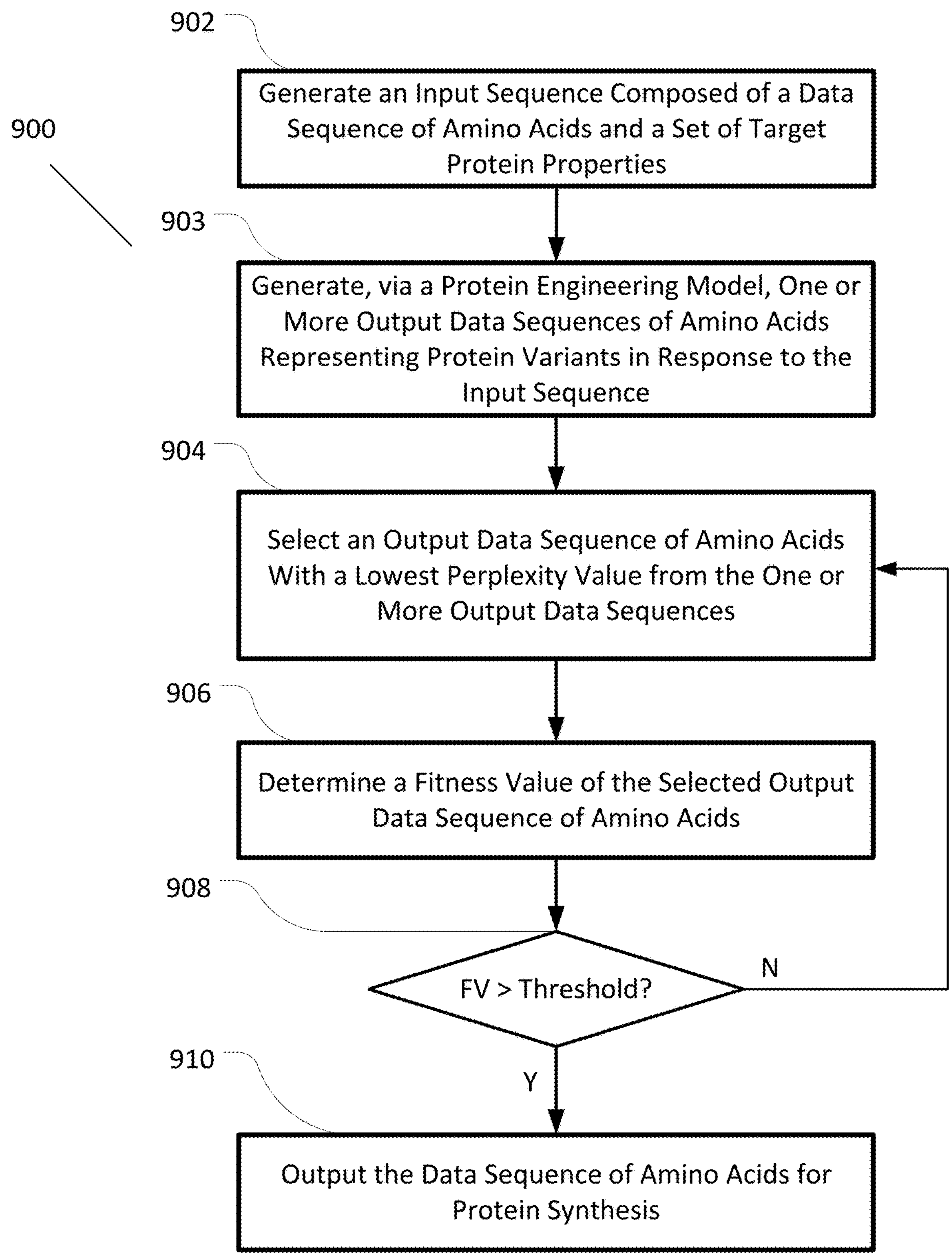
FIG. 9 is a simplified diagram of a method for quality control with zero-shot fitness selection for protein generation, according to some embodiments.

FIG. 9 is a simplified diagram of a method 900 for quality control with zero-shot fitness selection for protein generation, according to some embodiments. One or more of the processes of method 900 may be implemented, at least in part, in the form of executable code stored on non-transitory, tangible, machine-readable media that when run by one or more processors may cause the one or more processors to perform one or more of the processes. In some embodiments, method 900 corresponds to assessing, by the protein validation module 235, the functional properties of the data sequences of proteins generated by protein generation module 120 in FIG. 1.

One objective of protein engineering is to engineer functional proteins, e.g., the resulting generated data sequence 123 of amino acids would actually yield the target properties 105. Traditionally, protein engineering adopts directed evolution, which iterates through rounds of mutation and screening to converge at a high-fitness (e.g., functioning) protein. Some machine learning methods may aid in the subsequent rounds of directed evolution by in silico screening of proteins. These methods, however, still largely rely on random mutation in an exponentially large search space. In one embodiment, as the protein generation module 230 has learned the distribution of evolutionarily-relevant proteins, the protein generation module 230 may be expected to directly generate data sequences of amino acids that yield high-fitness proteins.

For example, a particular protein, protein G domain B1 (GB1) is used for binding to an antibody, which is important for the purification, immobilization, and detection of immunoglobulins (antibodies), proteins used by the immune system to neutralize pathogenic viruses and bacteria. Ideally, data sequences of amino acids are to be generated to form GB1 proteins with high binding affinity and stability. Possible variants of data sequences may include 149,361 of a total 160,000 possible variants from NNK/NNS saturation mutagenesis at four positions known to interact especially. Reported fitness values correspond to a measure of both stability (i.e. the fraction of folded proteins) and function (i.e. binding affinity to IgG-Fc) by coupling mRNA display with next-generation sequencing. Therefore, protein sequences with high fitness values are desired.

Method 900 starts at process 902, where an input sequence composed of a data sequence of amino acids and a set of target protein properties are generated, e.g., in a similar manner as process 702 in FIG. 7. At process 903, the protein engineering model generates one or more output data sequences of amino acids representing protein variants in response to the input sequence.

At process 904, an output data sequence of amino acids with the lowest perplexity value from the one or more output data sequences may be selected. For example, the perplexity may be a metric for language models, which is the exponentiated cross-entropy loss computed over each token in a dataset. Thus, high quality language models are expected to have low perplexities. For example, without supervised training of the protein generation model on the GB1 data or unsupervised fine-tuning of the protein generation model on a subset of similar immunoglobulin-binding protein data, each variant is passed through the protein generation model and select the top one hundred variants with the lowest perplexity values.

At process 906, the fitness value of the selected output data sequence of amino acids can then be determined. If the fitness value is higher than a threshold at process 908, the selected data sequence of amino acids may be outputted for protein synthesis at process 910. Otherwise, method 900 goes back to process 904 to select another output data sequence of amino acids with a low perplexity value.

Figure 10:
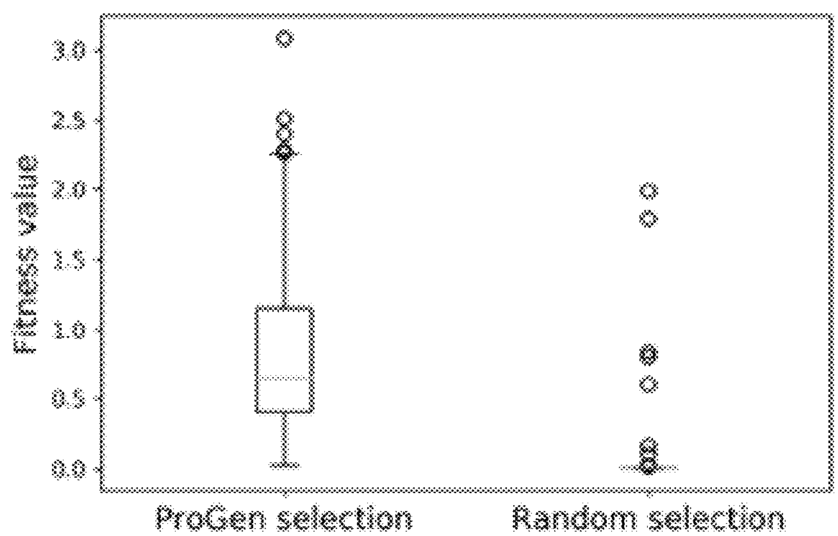
FIG. 10 provides an example data chart illustrating a comparison in fitness values of the data sequences generated and selected by the protein generation module, and random selection, according to one embodiment.

FIG. 10 provides an example data chart illustrating a comparison in fitness values of the data sequences generated and selected by the protein generation module 230, and random selection. In FIG. 10, the protein generation module exhibits higher fitness value performance in zero-shot selection of high-fitness protein sequences. In comparison, random mutation, which is the main technique used by directed evolution and machine learning assisted directed evolution, statistically generates samples with low fitness. Therefore, with effective sampling techniques, protein generation module 230 can be utilized to generate a spread of samples that yield statistically high fitness. These results imply that the protein generation module 230 trained by protein data provided by the protein language training module 232, has not only learned the distribution of structurally-relevant proteins, but also functionally-relevant proteins.

In addition to perplexity value, another metric to evaluate the performance of the protein generation module may be the mean per-token hard accuracy over the tokens in a sequence, which judges a prediction incorrect for any amino acid that is not the ground truth. Mean per-token soft accuracy relies on BLO-SUM62, a block substitution matrix that specifies which amino acid substitutions are more or less acceptable according to their frequency in known well-formed proteins. BLOSUM62 is widely used across adopted alignment software (e.g., BLAST2). For example, the mean per-token soft accuracy may use BLOSUM62 to penalize incorrect amino acid predictions according to the frequency of that substitution in the matrix. In this way, if the substitution is likely in nature, soft accuracy may penalize the model less.

To assess the quality of the data sequences outputted from the protein generation module, three levels of structures may be evaluated: (1) primary sequence similarity, (2) secondary structure accuracy, and (3) conformational energy analysis. For example, primary sequence similarity may be defined by a global, pairwise sequence alignment score computed with the Biopython package3. This score is based on the Needleman-Wunsch algorithm (Needleman et al, a general method applicable to the search for similarities in the amino acid sequence of two proteins. Journal of molecular biology, 48(3):443-453, 1970) informed by the BLOSUM62 substitution matrix. A gap open penalty of −0.5 and a gap continue penalty of −0.1 may be used. The resulting score is then normalized by the length of the protein. Experiments reporting sequence similarity are limited to test samples with a form of experimental evidence of X-ray/NMR crystallography, mass spectrometry, or existence in cDNA or RT-PCR to indicate transcript existence.

In one embodiment, secondary structure accuracy may be computed per-residue for predicted secondary structures by PSIPREDS with greater than 0.5 confidence. PSI-BLAST was performed on each generated sample to extract the Multiple Sequence Alignments (MSAs) with respect to the UniRef90 database proposed in Suzek et al., Uniref clusters: a comprehensive and scalable alternative for improving sequence similarity searches. Bioinformatics, 31(6):926-932, 2015. These MSAs were provided to PSIPRED for higher quality secondary structure prediction. Experiments reporting secondary structure accuracy were limited to test samples with high UniprotKB existence scores as described in the previous paragraph.

In one embodiment, conformational energy uses the Rosetta-RelaxBB protocol6. Rosetta-RelaxBB performs a Monte Carlo optimization of the Rosetta energy function over the space of amino acid types and rotamers. The Rosetta energy is based on biophysical laws and constraints. Between each design round, amino acid side-chains are replaced, while the carbon backbone torsions are kept fixed. Energy minimization/relaxation is performed after threading the amino acid sequence through the known structure. This allows the backbone to move, possibly into a lower energy state. A lower resulting Rosetta energy correlates to a more relaxed-state and viable conformation for a given protein sequence. Before applying the procedure above, the native template may be relaxed first. Experiments that report conformational energy are limited to test samples from SWISSPROT with associated 3D structures in RCSB PDB 7.

To assess generative quality, baselines are provided for different levels of random mutation. For a given sequence, a proportion (25-100%) of amino acids in the sequence is randomly substituted within one of the 20 standard amino acids other than itself. For conformational energy, we also include an all-alanine baseline (i.e. a sequence with only the amino acid alanine), as it is a non-bulky, chemically inert amino acid that mimics the existing secondary structure well when substituted. These baselines provide a scale across each of the above metrics. A particular random mutation may or may not have constructive or destructive effects on protein structure or function. But viewed in aggregate, the performance of the 100% mutation baseline for any metric indicates failed generation. As performance approaches 0%, generation statistically indicates a closer reflection to desired structural and functional properties.

Table 1 shows that the protein generation module is a high-quality language model according to per-token metrics on the training and test sets.

TABLE 1

Protein Generation Model Performance

| Model | Perplexity | Hard Accuracy |
|---|---|---|
| UNIFORM BASELINE | 25 | 4 |
| EMPIRICAL BASELINE | 18.14 | 6 |
| PROTEIN GENERATION | 8.56 | 45 |
| ID-TEST | 8.17 | 45 |
| OOD-TEST | 13.34 | 22 |
| OOD-TEST-20 (RANDOM) | 17.78 | 9 |
| OOD-TEST-20 (FINE-TUNED) | 7.45 | 50 |

Protein generation module generalizes to the full test set and achieves perplexities representative of a high-quality language model. Perplexities reported in Table 1 demonstrate that protein generation module dramatically improves over a uniform baseline, in which amino acids are sampled according to a uniform distribution, and an empirical baseline, in which amino acids are sampled according to the empirical frequencies in the training set. As a point of reference, state-of-the-art unidirectional language models for English Wikipedia achieve perplexities that range from 10 to 17 depending on model size (between 257M and 8.3B parameters) and whether training data was constrained to the English Wikipedia In addition, protein generation module generalizes to unseen protein families. The second section of Table 1 breaks this result into perplexities over the ID-test and OOD-test sets separately. Results on ID-test confirm that protein generation module generalizes well to sequences that belonged to protein families randomly sampled. As expected, performance is worse on the sequences in the OOD-test set, but the model still outperforms the empirical baseline for those held out protein families.

Fine-tuning protein generation module on unseen protein families improves over training from random initialization. The OOD-test is split into OOD-test-80 and OOD-test-20, fine-tuned protein generation module on OOD-test-80 until convergence (5 epochs; Adam; linear learning rate warmup to 1 k iterations) and retested on OOD-test-20. The third section of Table 1 shows that fine-tuning from protein generation module improves over training the same architecture with randomly initialized weights.

Figure 11:
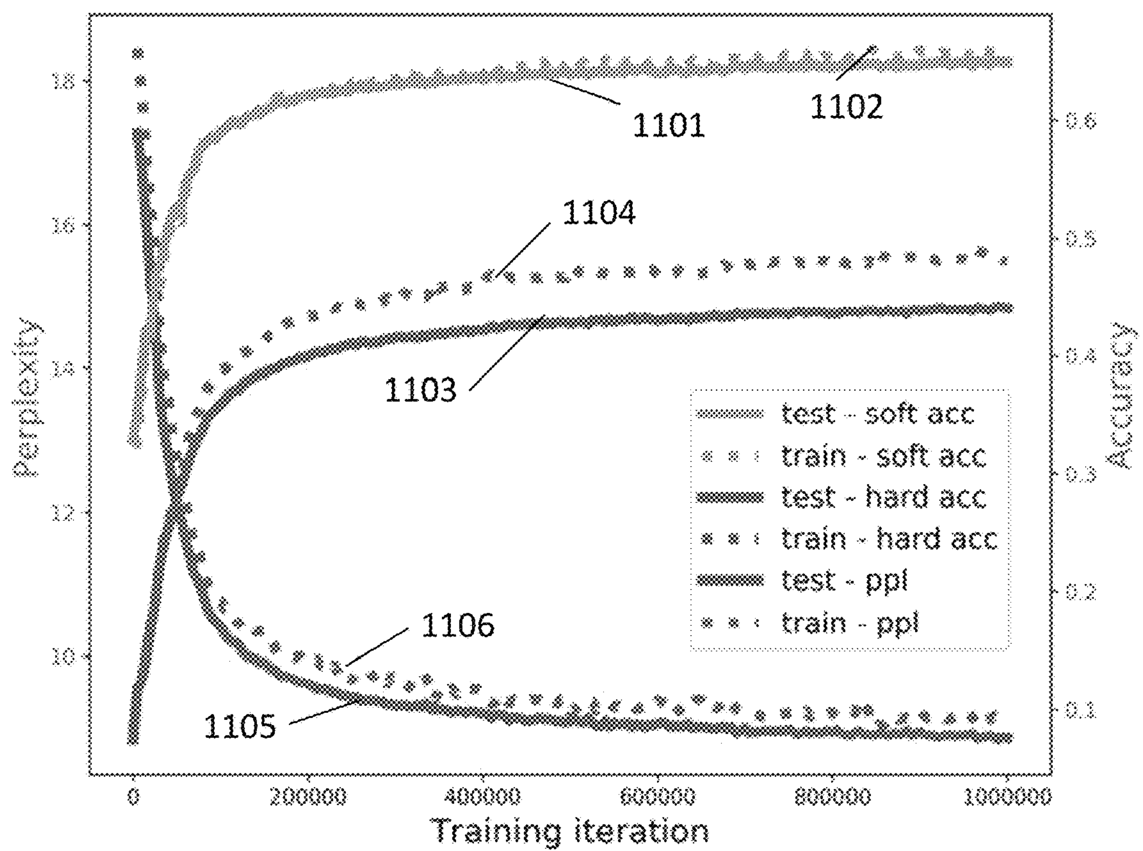
FIG. 11 provides an example data plot diagram illustrating the performance of training and testing sequences with the protein generation module, according to one embodiment.

FIG. 11 provides an example data plot diagram illustrating the performance of training and testing sequences with the protein generation module. BLOSUM62-informed soft accuracy shows no gap between training soft accuracy (shown at plot 1102) and testing soft accuracy (shown at plot 1101), while the training hard accuracy (shown at plot 1103) may be significantly higher than the testing hard accuracy (shown at plot 1104). This may suggest that hard accuracy hides the possibility that possible errors of the protein generation module may often correspond to amino acid substitutions found in nature. The perplexity value may be comparable between the testing (shown at plot 1105) and training performance (shown at plot 1106).

Figure 12:
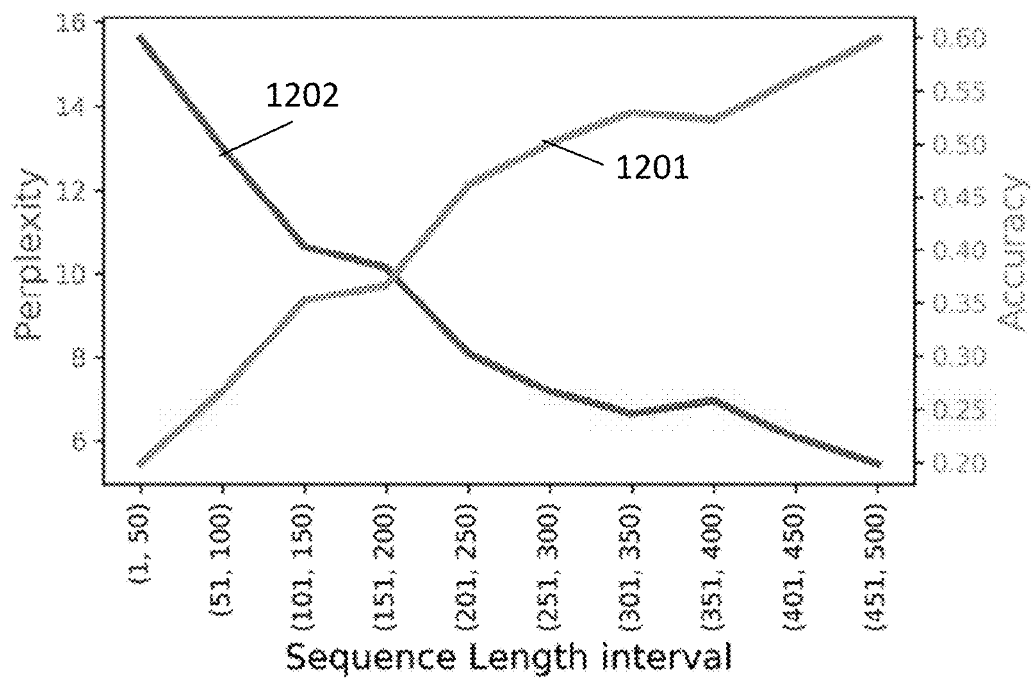
FIG. 12 provides an example data plot diagram illustrating the performance of the protein generation module per different sequence length intervals, according to one embodiment.

FIG. 12 provides an example data plot diagram illustrating the performance of the protein generation module per different sequence length intervals. Plot 1201 shows the mean per-token hard accuracy, and plot 1202 shows the mean perplexity value. The full test set performance may improve for later segments of sequences in keeping with the intuition that additional context supports better predictions, for intervals up to 500 tokens to ensure a minimum of 30*k* samples per interval.

Figure 13:
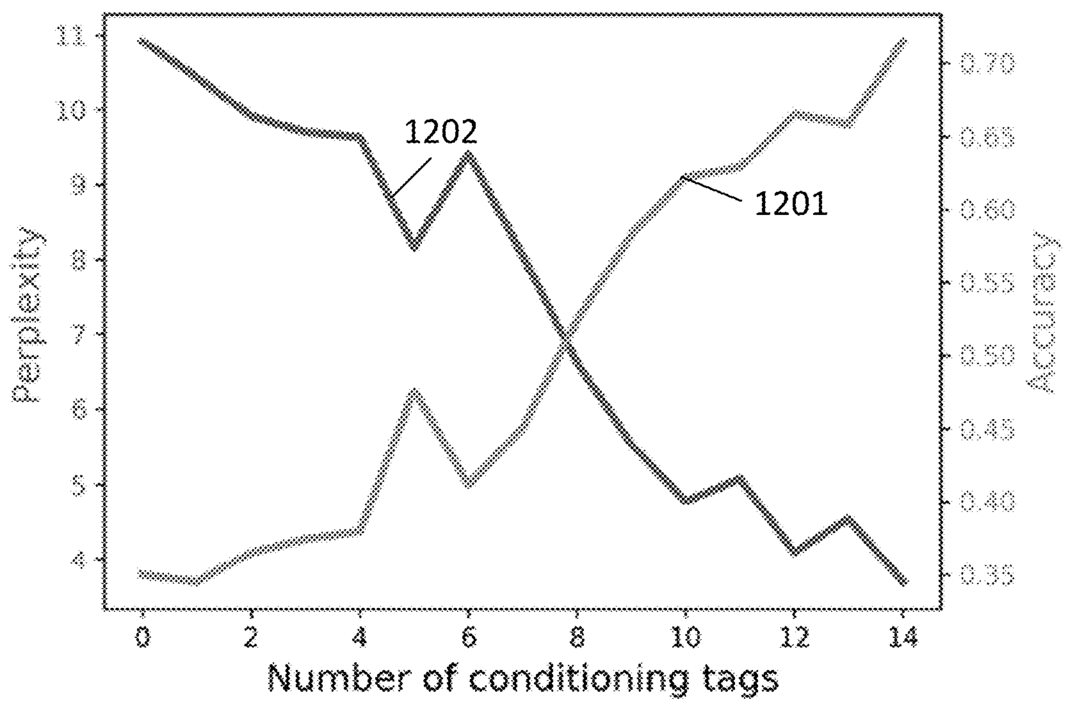
FIG. 13 provides an example data plot diagram illustrating the performance of the protein generation module per the number of conditional tags, according to one embodiment.

FIG. 13 provides an example data plot diagram illustrating the performance of the protein generation module per the number of conditional tags. Plot 1301 shows the mean accuracy per token, and plot 1302 shows the perplexity value. The full test set performance also improves as the number of conditioning tags associated with proteins increases, with up to 14 conditioning tags to ensure a minimum of 3 k samples per category.

Training curves further suggests that protein generation would benefit from even larger models and longer training. With 1B parameters, the protein generation module is comparable in size to the largest language models that have been publicly released for any modality, and, to the best of our knowledge, it is the largest model trained on amino acid sequences. FIG. 11 shows that despite its size and the amount of compute used to train, the protein generation module has yet to overfit the training data. This suggests that models for protein generation could still benefit from even larger models and additional compute.

BLOSUM62 soft accuracy reveals that protein prediction errors often follow natural amino acid substitutions that likely conserve higher level structure. Though the protein generation models proteins as pure sequences, protein function is more directly determined by the secondary and tertiary structures that these sequences encode in three-dimensional space. Model performance based on BLOSUM62 soft accuracy is more than 20% higher than using hard accuracy, which indicates that when the protein generation errors may often be substitutions that are acceptable in nature be-cause they still reflect the proper higher-level properties. This suggests that protein generation module has learned how to work within function-preserving mutational invariances.

Figure 14:
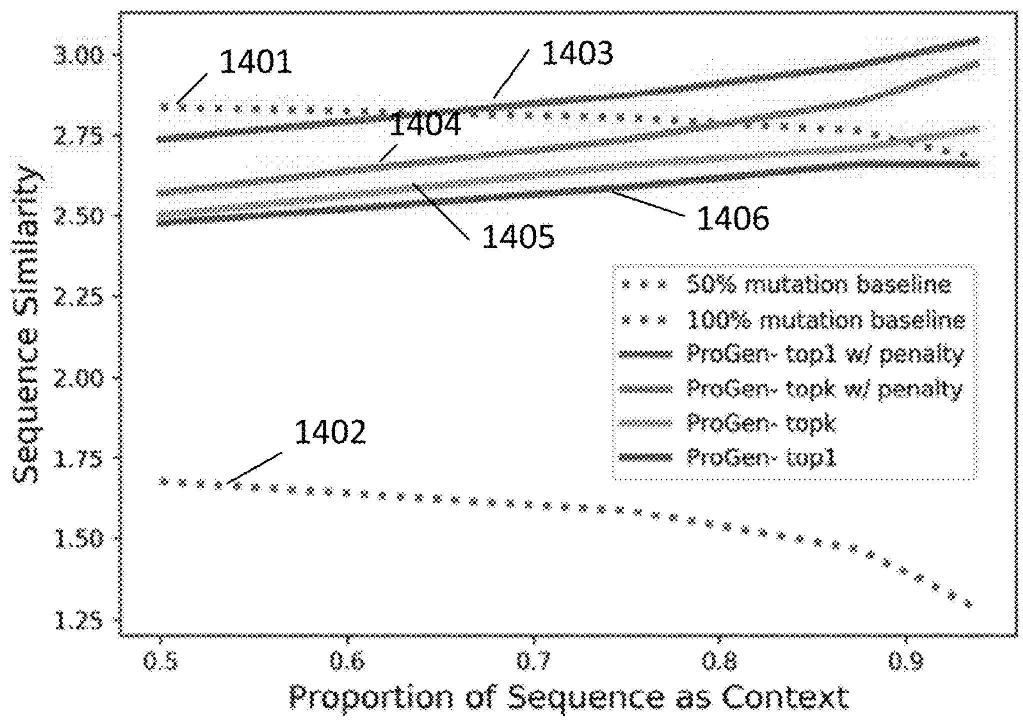
FIG. 14 provides an example data plot diagram depicting the results of experimenting with various combinations of top-k sampling and repetition penalties, according to one embodiment.

FIG. 14 provides an example data plot diagram depicting the results of experimenting with various combinations of top-k sampling and repetition penalties. Plot 1401 shows the sequence similarity for 50% mutation baseline; plot 1402 corresponds to the sequence similarity for 100% mutation baseline; plot 1403 corresponds to the protein generation module with top 1 sampling with penalty; plot 1404 corresponds to the protein generation module with top-k sapling with penalty; plot 1405 corresponds to the protein generation module with top-k sampling without penalty; and plot 1406 corresponds to the protein generation module with top-1 sampling without penalty. Over all context lengths, the protein generation module performs best with k=1 and the repetition penalty applied to recently generated amino acids. With this nearly greedy sampling, the protein generation module manages to generate proteins with sequence similarity comparable to randomly mutating 50% of the amino acids that are not seen in the given context.

Figure 15:
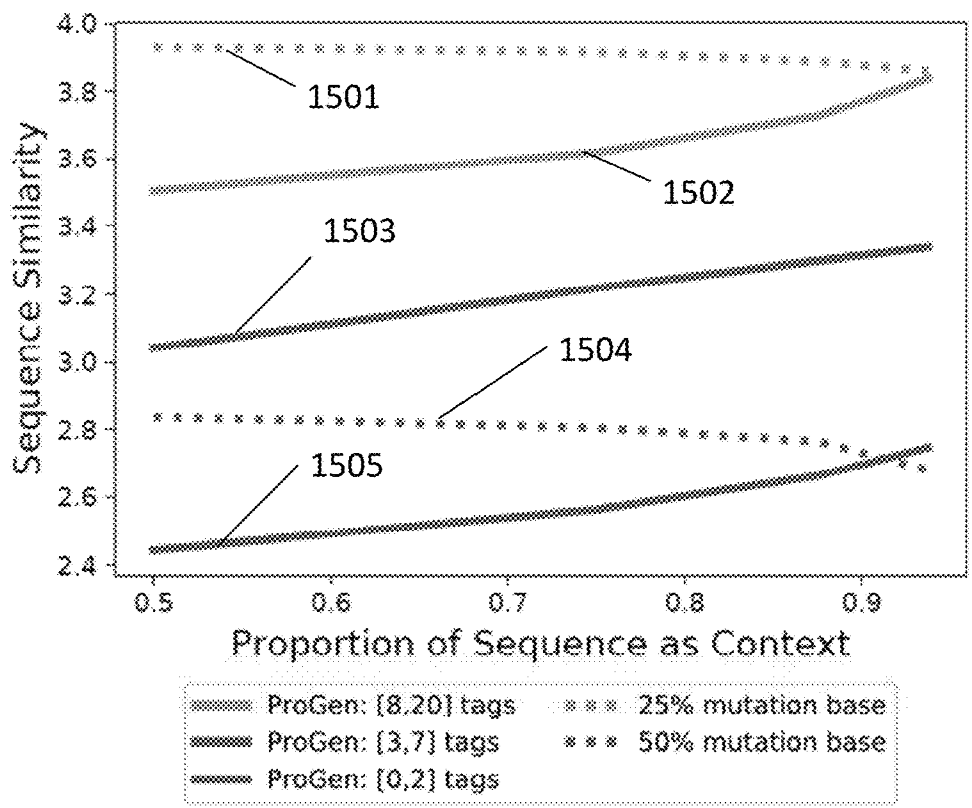
FIG. 15 provides an example data plot diagram depicting the results of experimenting with various proportion of sequence as context, according to one embodiment.
Figure 16:
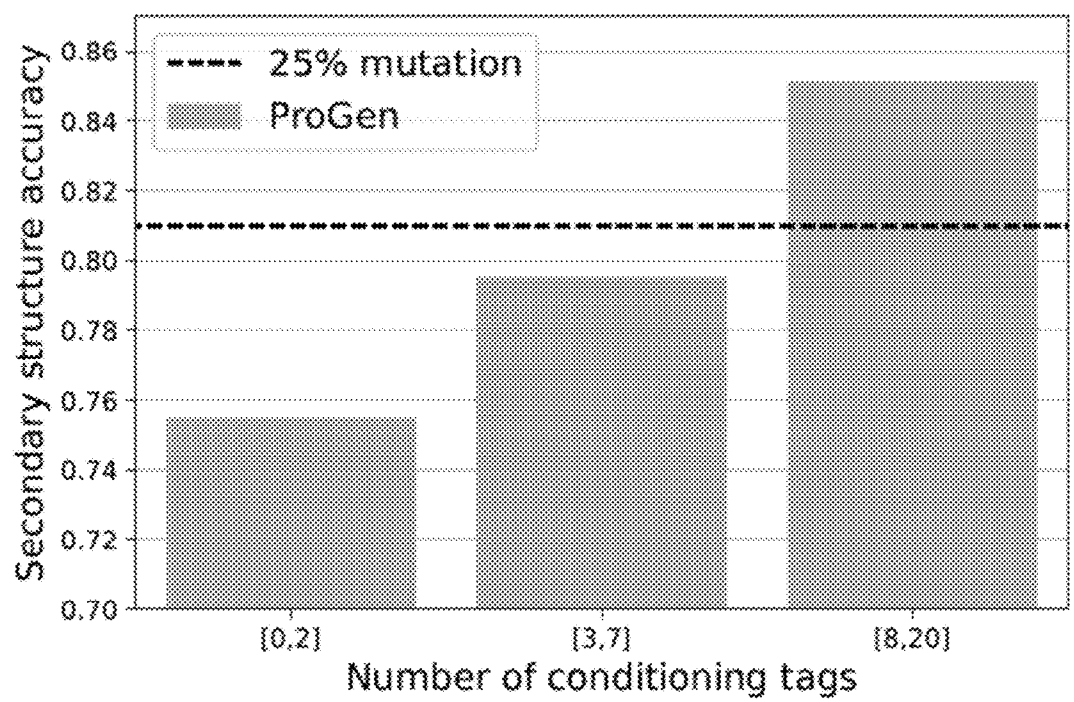
FIG. 16 provides an example data plot diagram depicting the results of experimenting with various different number of conditional tags evaluated by the secondary structure accuracy, according to one embodiment.

Sequence similarity suggests that the protein generation module merely approaches the 25% mutation baseline, but secondary structure accuracy suggests that the protein generation module surpasses it. FIG. 15 provides an example data plot diagram depicting the results of experimenting with various proportion of sequence as context. In FIG. 15, this sequence similarity across different numbers of conditioning tags are analyzed, where plot 1501 corresponds to 25% mutation base, plot 1502 corresponds to protein generation module using 8-20 tags, plot 1503 corresponds to protein generation module using 3-7 tags, plot 1504 corresponds to 50% mutation base, and plot 1505 corresponds to the protein generation module using 0-2 tags. Sequences associated with at least 3 conditioning tags begin to exceed the 50% mutation baseline, and as amino acid context increases, sequences with at least 8 conditioning tags approach the 25% mutation baseline. Notably, even in the best case, according to sequence similarity, the protein generation module doesn't surpass the 25% mutation baseline. By contrast, according to secondary structure accuracy, sequences with at least 8 conditioning tags surpass the 25% mutation baseline, as shown in FIG. 16. This discrepancy between sequence similarity and secondary structure accuracy further corroborates the evaluation that errors registered by lower-level metrics often correspond to acceptable substitutions according to higher-level metrics that more directly correspond to functional viability.

Figure 17:
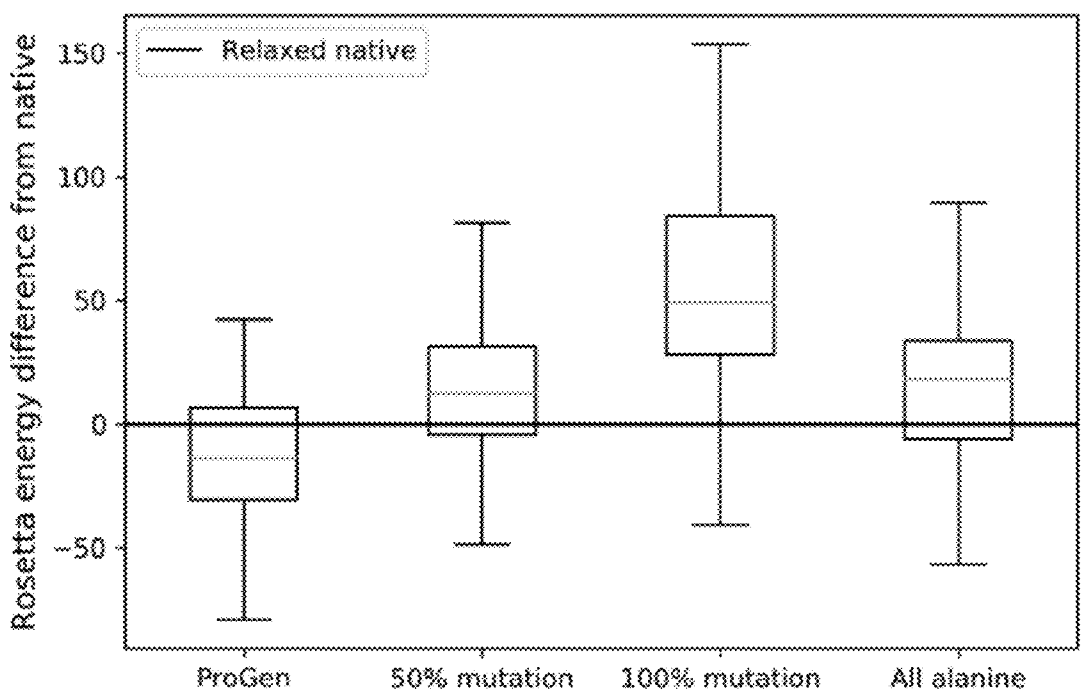
FIG. 17 shows the differences between the energy levels of various mutated versions of native proteins and protein generation module samples, according to one embodiment.

After threading and relaxation, samples generated by the protein generation module are likely to exhibit desired structure and function. As a measure of generation quality, the protein generation module sequences may be threaded through known structures and examine if they exhibit favorable, low energy states. FIG. 17 shows the differences between the energy levels of native proteins, protein generation module samples, the native proteins with 50% and 100% of amino acids randomly mutated, as well as the all-alanine baseline. Proteins completed by the protein generation module may be much closer to the energy levels of the native protein than all baselines. Generated samples exhibit energy levels near or even below their associated relaxed native templates.

Figure 18:
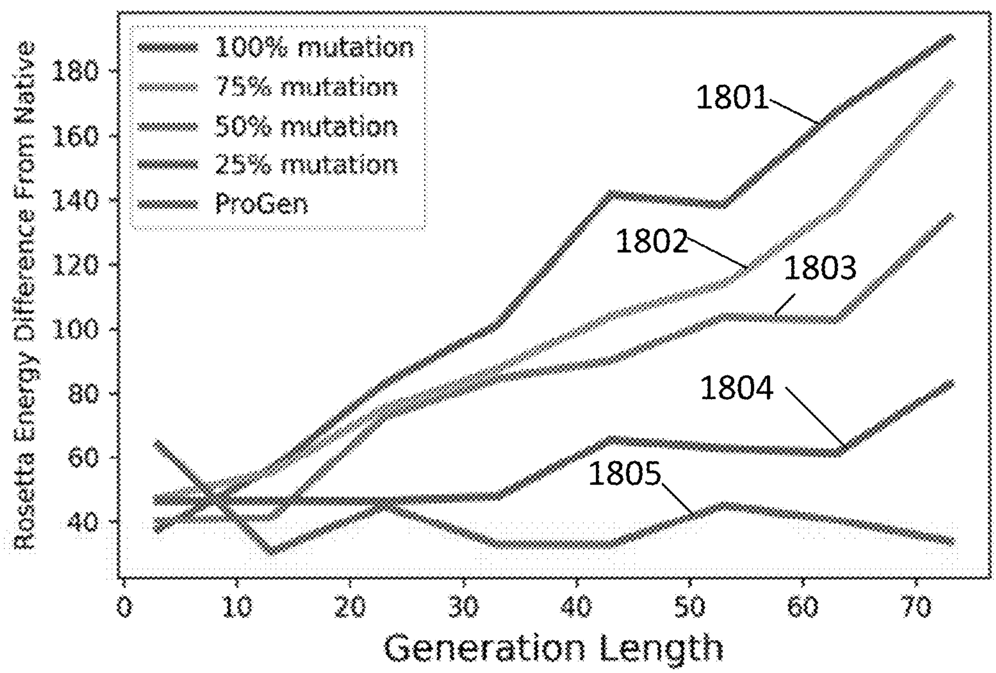
FIG. 18 shows an example data plot diagram illustrating the completion quality for protein VECFR2, according to one embodiment.

FIG. 18 shows an example data plot diagram illustrating the completion quality for protein VEGFR2. VEGFR2 is a protein responsible for fundamental cell processes such as cell proliferation, survival, migration, and differentiation. VEGFR2 was excluded from training as a subsequence belongs to a held out protein family in out-of-distribution test. In a protein completion task, the protein generation module may intake the amino acid sequence beginning at residue 806 and ending at residue 1168 of VEGFR2 (PDB ID: 2XIR). For different generation lengths, the protein generation module may sample amino acids to complete the sequence up to residue 1168 with the remainder of the sequence provided as context. In FIG. 18, plot 1801 corresponds to the Rosetta energy difference from native corresponding to 100% mutation, plot 1802 corresponds to the Rosetta energy difference from native corresponding to 75% mutation, plot 1803 corresponds to the Rosetta energy difference from native corresponding to 50% mutation, plot 1804 corresponds to the Rosetta energy difference from native corresponding to 25% mutation, and plot 1805 corresponds to the Rosetta energy difference from native corresponding to the protein generation module. FIG. 18 shows that the conformational energy calculated after threading and relaxation of the protein generation module samples are lower compared to all baselines, indicating better structural conservation. The generated samples across FIG. 18 exhibit a mean sequence identity of 73.1% with the native sequence. This correlates to a lower sequence identity than the 25% mutation baseline (74% identity) but with better Rosetta energies. This suggests meaningful deviation from the native protein while achieving the ultimate goal of preserving low energy.

Figure 19:
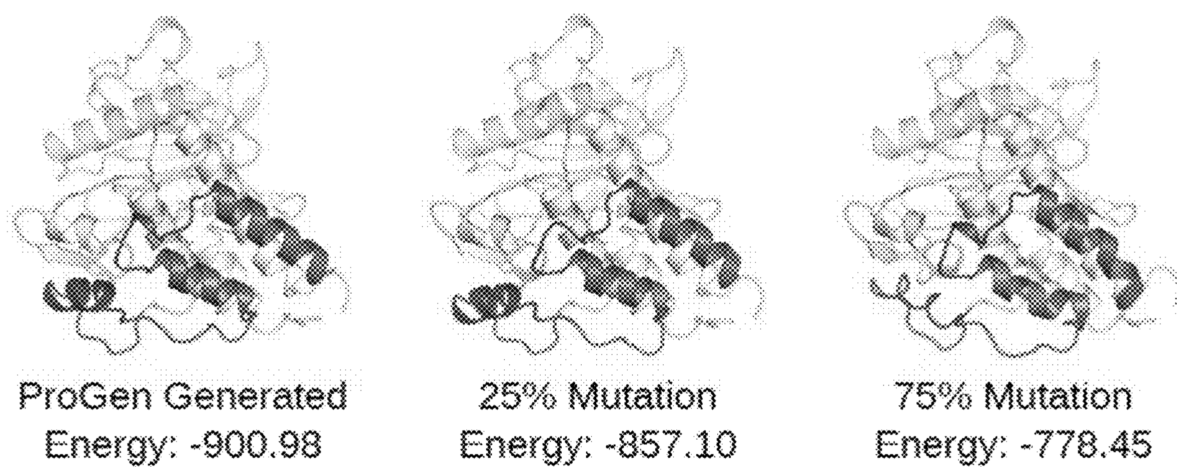
FIG. 19 provides illustrative samples comparing one sample generated via the protein generation module and samples from different mutation baselines, according to one embodiment.

FIG. 19 provides illustrative samples comparing one sample generated via the protein generation module and samples from each of the 25% and 75% mutation baselines. The protein generation module sample exhibits lower energy overall, and energy is highest for amino acids that do not have secondary structure. This suggests that the protein generation module has learned to prioritize the most structurally important segments of the protein.

Figure 20:
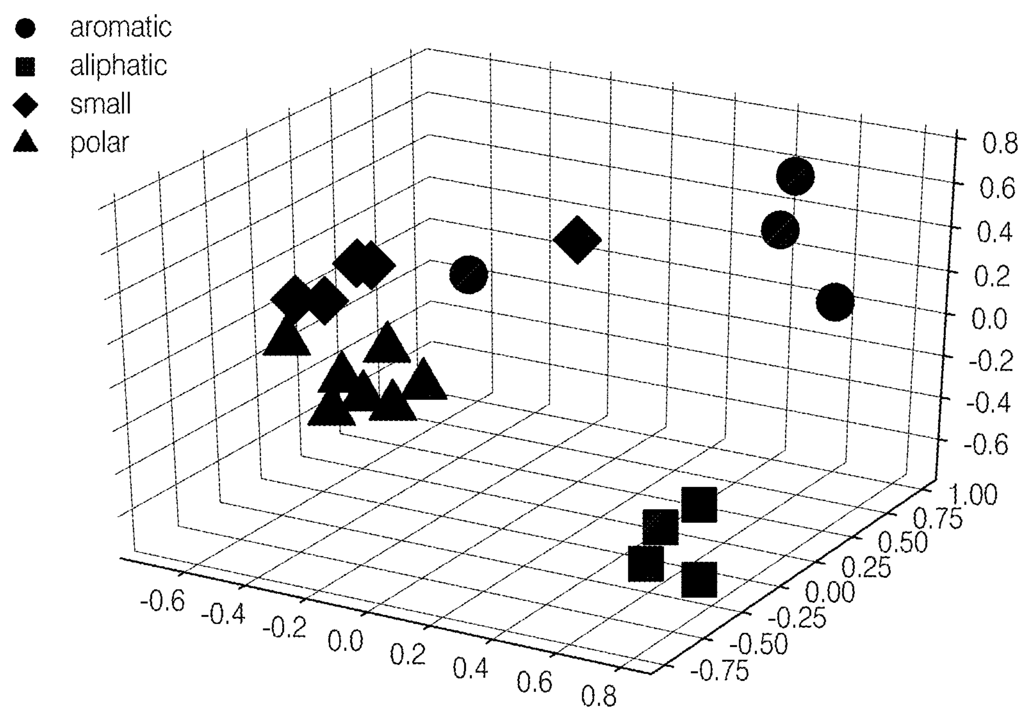
FIG. 20 provides an example data plot diagram illustrating the trained embedding weights for the standard amino acids tokens that are reduced to three dimensions with principle component analysis (PCA), according to one embodiment.

In one embodiment, the protein generation module was trained from a randomly initialized embedding layer with no prior knowledge of residue biochemical properties. Through per-token training on millions of protein sequences, the protein generation module seems to have inherently learned the natural clustering of amino acids that align with biophysicochemical properties. FIG. 20 provides an example data plot diagram illustrating the trained embedding weights for the standard amino acids tokens that are reduced to three dimensions with principle component analysis (PCA).

Figure 21:
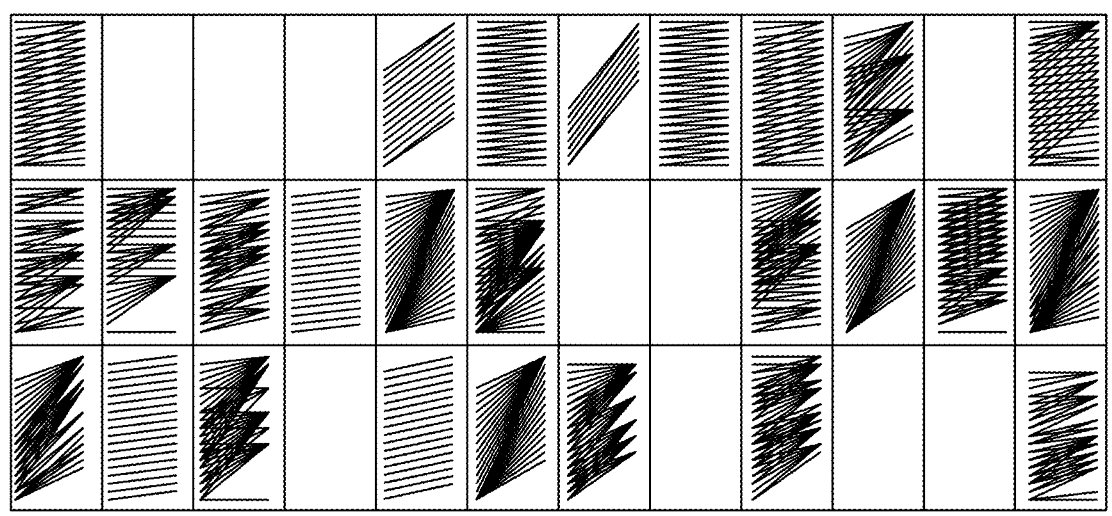
FIGS. 21-22 provide example visualizations of the attention head patterns of the protein generation module, according to one embodiment.
Figure 22:
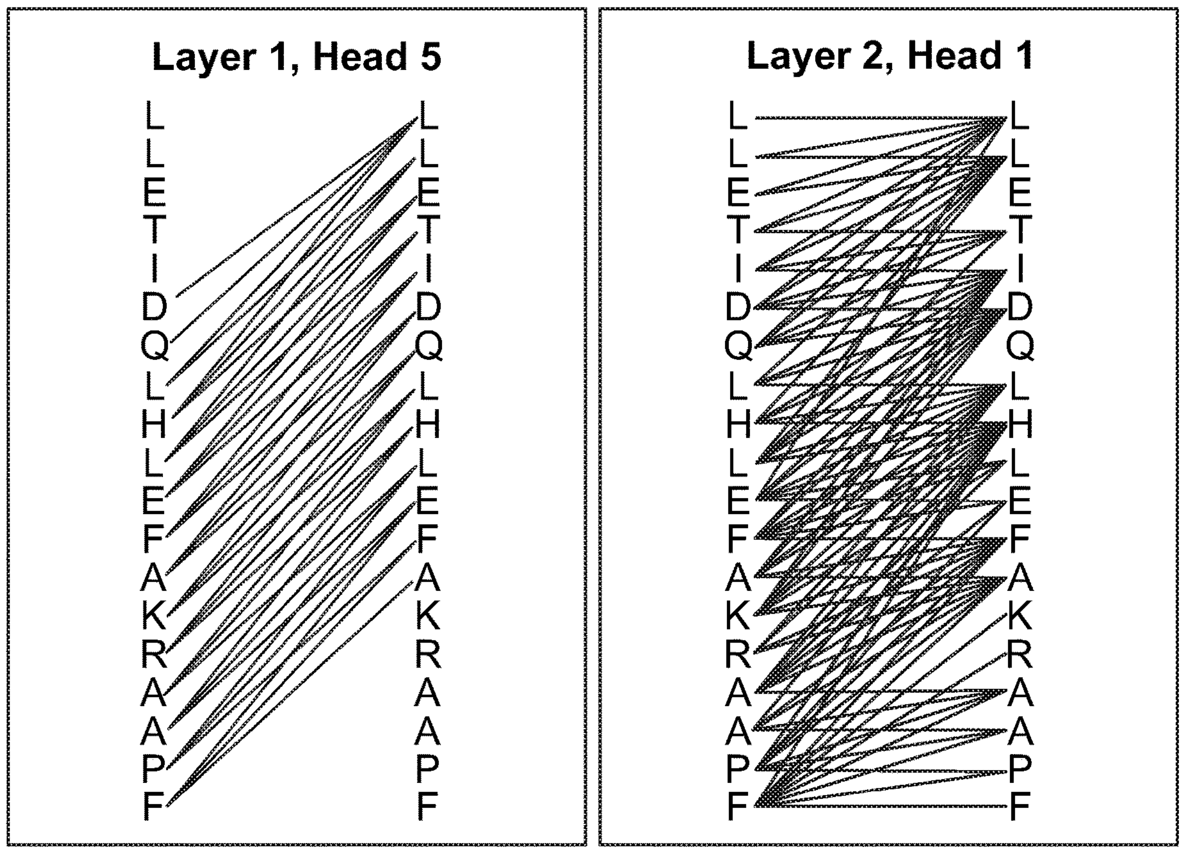

FIGS. 21-22 provide example visualizations of the attention head patterns of the protein generation module. For both FIGS. 21-22, the attention weight patterns are visualized in each head of the protein generation module for α-actinin protein (PDB: 4D1E) residues 510 to 528, which exhibits an alpha helical structure. In FIG. 21, layers 1 to 3 and attention heads 1 to 12 of the protein generation module are visualized. The attention mechanism exhibits well-differentiated local and global patterns which may indicate specialization of each head on different tasks. In FIG. 22, local attention pattern for two example attention heads are shown. The lines indicate attentions to previous tokens for a given predicted token.

Therefore, the protein generation module provides a controllable protein generation language model trained on the full evolutionary diversity of one of the largest sequence databases. The model generates proteins that exhibit near native structure energies which likely implies functional viability. The protein generation module has the potential to play a new, complementary role alongside other state-of-the-art methods in protein engineering. For example, in directed evolution, initial sequences may be sampled from the protein generation module according to desired conditioning tags. In later rounds of evolution, protein completion with context for particular residue spans, or hotspots, may provide higher fitness samples. In de novo protein design, using the protein generation module with conditioning tags may allow for designing new proteins with existing folding motifs in new protein families or host organisms. This same strategy may be used in conjunction with threading and structure-based protein design. Because conditioning tags orient protein generation module in sequence space, the protein generation module may even be used as a model to sample from the distribution of evolutionarily viable proteins near one particular protein. This may provide useful augmentations around data for non-homologous domains where existing techniques, such as MSAs, fall short.

Some examples of computing devices, such as computing device 200 may include non-transitory, tangible, machine readable media that include executable code that when run by one or more processors (e.g., processor 210) may cause the one or more processors to perform the processes of methods 600-900. Some common forms of machine readable media that may include the processes of methods 600-900 are, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

This description and the accompanying drawings that illustrate inventive aspects, embodiments, implementations, or applications should not be taken as limiting. Various mechanical, compositional, structural, electrical, and operational changes may be made without departing from the spirit and scope of this description and the claims. In some instances, well-known circuits, structures, or techniques have not been shown or described in detail in order not to obscure the embodiments of this disclosure Like numbers in two or more figures represent the same or similar elements.

In this description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the invention should be limited only by the following claims, and it is appropriate that the claims be construed broadly and in a manner consistent with the scope of the embodiments disclosed herein.

What is claimed is:

1. A method for training a neural network based language model for generating a new protein sequence having target protein properties, the method comprising:

obtaining, via a communication interface and over a network from one or more databases, a training dataset of data sequences of amino acids representing sample proteins;

forming a set of conditional tags representing protein properties of a sample data sequence of amino acids based on metadata in the training dataset;

generating, from the training dataset, an updated training dataset comprising an input training sequence concatenating the sample data sequence of amino acids and the formed set of conditional tags;

training the neural network based language model implemented on one or more hardware processors for generating the new protein sequence using the updated training dataset by:

generating, via the neural network based language model, a next-token prediction distribution for a next token in a predicted protein sequence from the input training sequence conditioned on previously generated tokens and the formed set of conditional tags;

computing a loss metric based on generated next-token prediction distributions in the predicted protein sequence and tokens corresponding to the sample of data sequence of amino acids over the updated training dataset;

updating the neural network based language model using the computed loss metric via backpropagation;

generating, by the trained neural network based language model, the new protein sequence based on one or more input conditional tags representing the target protein properties; and transmitting, via the communication interface, the new protein sequence to a protein synthesis facility thereby causing protein synthesis based on the new protein sequence.

2. The method of claim 1, wherein the forming the set of conditional tags representing protein properties of the sample data sequence of amino acids based on metadata in the training dataset comprises:

dividing the set of conditional tags into a first set of keyword tags and a second set of taxonomic tags.

3. The method of claim 1, wherein the training dataset is split into a primary training dataset, an out-of-distribution training dataset representing a held-out protein family, and an in-distribution training dataset representing randomly sampled proteins.

4. The method of claim 1, wherein the input training sequence includes the sample sequence of amino acids and an inverse of the sample sequence of amino acids.

5. The method of claim 1, wherein the input training sequence is generated by:

retrieving the sample sequence of amino acids associated with a first set of conditional tags from a first database;

retrieving the sample sequence of amino acids associated with a second set of conditional tags from a second database; and randomly sampling one of the first set and the second set of conditional tags with a bias toward manually verified conditional tags.

6. The method of claim 1, wherein the set of conditional tags is applied with dropout with a pre-defined rate.

7. The method of claim 1, further comprising:

generating another input training sequence comprising the sample data sequence of amino acids without any conditional tags.

8. The method of claim 1, further comprising:

truncating the input training sequence to a pre-defined length.

9. The method of claim 1, wherein the loss metric is a sum of negative log-likelihoods corresponding to the generated next-token prediction distributions by the neural network based language model in response to at least the input training sequence in the updated training dataset.

10. A system for training a neural network based language model for generating a new protein sequence having target protein properties, the system comprising:

a communication interface configured to obtain, over a network from one or more databases, a training dataset of data sequences of amino acids representing sample proteins;

a memory configured to store parameters of the neural network based language model and a plurality of processor-executable instructions; and a processor configured to read and execute the processor-executable instructions, wherein the instructions are configured to:

form a set of conditional tags representing protein properties of a sample data sequence of amino acids based on metadata in the training dataset;

generate, from the training dataset, an updated training dataset comprising an input training sequence concatenating the sample data sequence of amino acids and the formed set of conditional tags;

train the neural network based language model implemented on one or more hardware processors for generating the new protein sequence using the updated training dataset by:

generating, via the neural network based language model, a next-token prediction distribution from the input training sequence conditioned on previously generated tokens;

computing a loss metric based on each respective generated next-token prediction distributions corresponding to at least the input training sequence of amino acids over the updated training dataset; and updating the parameters of the neural network based language model using the computed loss metric; and generate, by the trained neural network based language model, the new protein sequence based on one or more input conditional tags representing the target protein properties; and transmit, via the communication interface, the new protein sequence to a protein synthesis facility thereby causing protein synthesis based on the new protein sequence.

11. The system of claim 10, wherein the processor is configured to form the set of conditional tags representing protein properties of the sample data sequence of amino acids based on metadata in the training dataset by:

dividing the set of conditional tags into a first set of keyword tags and a second set of taxonomic tags.

12. The system of claim 10, wherein the training dataset is split into a primary training dataset, an out-of-distribution training dataset representing a held-out protein family, and an in-distribution training dataset representing randomly sampled proteins.

13. The system of claim 10, wherein the input training sequence includes the sample sequence of amino acids and an inverse of the sample sequence of amino acids.

14. The system of claim 10, wherein the input training sequence is generated by:

retrieving the sample sequence of amino acids associated with a first set of conditional tags from a first database;

retrieving the sample sequence of amino acids associated with a second set of conditional tags from a second database; and randomly sampling one of the first set and the second set of conditional tags with a bias toward manually verified conditional tags.

15. The system of claim 10, wherein the set of conditional tags is applied with dropout with a pre-defined rate.

16. The system of claim 10, wherein the processor is further configured to:

generate another input training sequence comprising the sample data sequence of amino acids without any conditional tags.

17. The system of claim 10, wherein the processor is further configured to:

truncate the input training sequence to a pre-defined length.

18. The system of claim 10, wherein the loss metric is a sum of negative log-likelihoods corresponding to the generated next-token prediction distributions by the neural network based language model in response to at least the input training sequence in the updated training dataset.

19. A non-transitory processor-executable storage medium storing processor-executable instructions for training a neural network based language model for generating a new protein sequence having target protein properties, the processor-executable instructions being executable by a processor to perform:

obtaining, via a communication interface and over a network from one or more databases, a training dataset of data sequences of amino acids representing sample proteins;

forming a set of conditional tags representing protein properties of a sample data sequence of amino acids based on metadata in the training dataset;

generating, from the training dataset, an updated training dataset comprising an input training sequence concatenating the sample data sequence of amino acids and the formed set of conditional tags;

training the neural network based language model implemented on one or more hardware processors for generating the new protein sequence using the updated training dataset by:

generating, via the neural network based language model, a next-token prediction distribution from the input training sequence conditioned on previously generated tokens;

computing a loss metric based on generated next-token prediction distributions corresponding to at least the input training sequence of amino acids over the updated training dataset; and updating the neural network based language model using the computed loss metric via backpropagation;

generating, by the trained neural network based language model, the new protein sequence based on one or more input conditional tags representing the target protein properties; and transmitting, via the communication interface, the new protein sequence to a protein synthesis facility thereby causing protein synthesis based on the new protein sequence.

20. The medium of claim 19, wherein the input training sequence is generated by:

retrieving the sample sequence of amino acids associated with a first set of conditional tags from a first database;

retrieving the sample sequence of amino acids associated with a second set of conditional tags from a second database; and randomly sampling one of the first set and the second set of conditional tags with a bias toward manually verified conditional tags.

* * * * *